(12) United States Patent
Sarge

(10) Patent No.: US 11,191,554 B2
(45) Date of Patent: Dec. 7, 2021

(54) VASCULAR RE-ENTRY DEVICE

(71) Applicant: C. R. Bard, Inc., Franklin Lakes, NJ (US)

(72) Inventor: Jeff Sarge, Fremont, CA (US)

(73) Assignee: C.R. Bard, Inc., Franklin Lakes, NJ (US)

(*) Notice: Subject to any disclaimer, the term of this patent is extended or adjusted under 35 U.S.C. 154(b) by 324 days.

(21) Appl. No.: 16/437,457

(22) Filed: Jun. 11, 2019

(65) Prior Publication Data

US 2019/0290304 A1    Sep. 26, 2019

Related U.S. Application Data

(63) Continuation of application No. 15/413,259, filed on Jan. 23, 2017, now Pat. No. 10,357,263, which is a continuation of application No. 14/365,016, filed as application No. PCT/US2012/021766 on Jan. 18, 2012, now Pat. No. 9,603,615.

(51) Int. Cl.
| | |
|---|---|
| A61B 17/22 | (2006.01) |
| A61F 2/958 | (2013.01) |
| A61B 50/13 | (2016.01) |
| A61M 29/00 | (2006.01) |

(Continued)

(52) U.S. Cl.
CPC .... *A61B 17/2202* (2013.01); *A61B 17/22012* (2013.01); *A61B 17/320068* (2013.01); *A61B 50/13* (2016.02); *A61F 2/958* (2013.01); *A61M 29/00* (2013.01); *A61B 2017/003* (2013.01); *A61B 2017/00778* (2013.01); *A61B 2017/22014* (2013.01); *A61B 2017/22095* (2013.01); *A61B 2017/32007* (2017.08); *A61B 2017/320056* (2013.01); *A61B 2017/320069* (2017.08);

(Continued)

(58) Field of Classification Search
CPC ...... A61B 17/320068; A61B 17/22012; A61B 2017/00778; A61B 2017/22014; A61B 2017/003; A61B 2017/22095; A61M 29/00; A61F 2/958; A61F 2250/0093
See application file for complete search history.

(56) References Cited

U.S. PATENT DOCUMENTS

| | | | |
|---|---|---|---|
| 3,296,620 | A | 1/1967 | Rodda |
| 3,433,226 | A | 3/1969 | Boyd |

(Continued)

FOREIGN PATENT DOCUMENTS

| | | |
|---|---|---|
| AU | 2007240154 A1 | 1/2008 |
| DE | 2256127 A1 | 5/1974 |

(Continued)

OTHER PUBLICATIONS

Japanese Office Action for Japanese Application No. 2010-134566, dated Mar. 2, 2012.

(Continued)

*Primary Examiner* — Julian W Woo
(74) *Attorney, Agent, or Firm* — Dinsmore & Shohl LLP

(57) ABSTRACT

A method for operating an ultrasonic reentry device, includes: providing an ultrasound transmission member having a proximal end and a distal end; providing a catheter body having a lumen surrounding the ultrasound transmission member; providing a dilator slidably disposed within the lumen of the catheter body, the dilator surrounding the ultrasound transmission member; and exposing the distal end of the ultrasound transmission member from a distal end of the dilator.

20 Claims, 17 Drawing Sheets

(51) Int. Cl.
*A61B 17/32* (2006.01)
*A61B 17/00* (2006.01)

(52) U.S. Cl.
CPC ............ *A61B 2017/320071* (2017.08); *A61F 2250/0093* (2013.01)

(56) References Cited

U.S. PATENT DOCUMENTS

| | | |
|---|---|---|
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,449,532 A | 5/1984 | Storz |
| 4,486,680 A | 12/1984 | Bonnet et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,781,186 A | 11/1988 | Simpson et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A | 8/1993 | Takasu |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,287,858 A | 2/1994 | Hammerslag et al. |
| 5,290,229 A | 3/1994 | Paskar |
| 5,304,115 A | 4/1994 | Pflueger et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |
| 5,507,738 A | 4/1996 | Ciervo |
| 5,516,043 A | 5/1996 | Manna et al. |
| 5,527,273 A | 6/1996 | Manna et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |

(56) References Cited

U.S. PATENT DOCUMENTS

| | | |
|---|---|---|
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,665,062 A | 9/1997 | Houser |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,725,494 A | 3/1998 | Brisken |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,127 A | 11/1998 | DeCastro |
| 5,830,222 A | 11/1998 | Makower |
| 5,846,218 A | 12/1998 | Brisken et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,004,335 A | 12/1999 | Vaitekunas et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,036,689 A | 3/2000 | Tu et al. |
| 6,051,010 A | 4/2000 | DiMatteo et al. |
| 6,066,135 A | 5/2000 | Honda |
| 6,113,558 A | 9/2000 | Rosenschein et al. |
| 6,120,515 A | 9/2000 | Rogers et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,298,620 B1 | 10/2001 | Hatzinikolas |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,737 B1 | 9/2002 | Nita et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,514,249 B1 | 2/2003 | Maguire et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,547,788 B1 | 4/2003 | Maguire et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,610,077 B1 | 8/2003 | Hancock et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |

(56) References Cited

U.S. PATENT DOCUMENTS

| | | |
|---|---|---|
| 6,733,451 B2 | 5/2004 | Rabiner et al. |
| 6,758,846 B2 | 7/2004 | Goble et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,758,510 B2 | 7/2010 | Nita et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,083,727 B2 | 12/2011 | Kugler et al. |
| 8,133,236 B2 | 3/2012 | Nita |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'connor |
| 8,308,677 B2 | 11/2012 | Nita et al. |
| 8,414,543 B2 | 4/2013 | Mcguckin, Jr. et al. |
| 8,506,519 B2 | 8/2013 | Nita |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 | 2/2014 | Nita et al. |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,764,700 B2 | 7/2014 | Zhang et al. |
| 8,768,433 B2 | 7/2014 | Jenkins et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 | 9/2016 | Nita et al. |
| 9,770,250 B2 | 9/2017 | Nita et al. |
| 9,955,994 B2 | 5/2018 | Nita |
| 10,004,520 B2 | 6/2018 | Nita et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0164030 A1 | 8/2004 | Lowe et al. |
| 2004/0167511 A1 | 8/2004 | Buehlmann et al. |
| 2004/0193033 A1 | 9/2004 | Badehi et al. |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0206039 A1 | 9/2006 | Wilson et al. |
| 2006/0264809 A1 | 11/2006 | Hansmann et al. |
| 2007/0032749 A1 | 2/2007 | Overall et al. |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2008/0294037 A1 | 11/2008 | Richter |
| 2009/0017293 A1 | 1/2009 | Arai et al. |
| 2010/0004558 A1 | 1/2010 | Frankhouser et al. |
| 2010/0023037 A1 | 1/2010 | Nita et al. |
| 2010/0076454 A1 | 3/2010 | Bos |
| 2010/0121144 A1 | 5/2010 | Farhadi |
| 2011/0105960 A1 | 5/2011 | Wallace |
| 2011/0130834 A1 | 6/2011 | Wilson et al. |
| 2011/0196399 A1 | 8/2011 | Robertson et al. |
| 2011/0196403 A1 | 8/2011 | Robertson et al. |
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0311844 A1 | 12/2012 | Nita et al. |
| 2012/0330196 A1 | 12/2012 | Nita |
| 2013/0060169 A1 | 3/2013 | Yamada |
| 2014/0236118 A1 | 8/2014 | Unser et al. |
| 2014/0243712 A1 | 8/2014 | Humayun et al. |
| 2014/0350401 A1 | 11/2014 | Sinelnikov |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0150571 A1 | 6/2015 | Nita et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0135835 A1 | 5/2016 | Onuma |
| 2016/0183956 A1 | 6/2016 | Nita |
| 2016/0271362 A1 | 9/2016 | Van Liere |
| 2016/0328998 A1 | 11/2016 | Nita et al. |
| 2016/0338722 A1 | 11/2016 | Nita et al. |
| 2016/0367284 A1 | 12/2016 | Nita et al. |
| 2017/0065288 A1 | 3/2017 | Imai et al. |
| 2017/0354428 A1 | 12/2017 | Nita et al. |
| 2018/0168668 A1 | 6/2018 | Zheng |
| 2018/0177515 A1 | 6/2018 | Boyle et al. |

(56) References Cited

U.S. PATENT DOCUMENTS

| | | |
|---|---|---|
| 2018/0221040 A1 | 8/2018 | Roll Hoye |
| 2018/0280005 A1 | 10/2018 | Parmentier |
| 2018/0280044 A1 | 10/2018 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 3705739 A1 | 9/1987 |
| WO | 3705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | 02094103 A1 | 11/2002 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2005112770 A1 | 12/2005 |
| WO | 2006049593 A1 | 5/2006 |
| WO | 2014022716 A2 | 2/2014 |
| WO | 2014105754 A1 | 7/2014 |
| WO | 2014106847 A1 | 7/2014 |
| WO | 20180187159 A1 | 10/2018 |

OTHER PUBLICATIONS

Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
Noone, D.: Experimental and Numerical Investigation of Wire Waveguides for Therapeutic Ultrasound Angioplasty. M.Eng. Dublin City University. 2008.
Definition of the term "connected", retrieved on Sep. 21, 2013. <www.thefreedictionary.com/connected> 1 page total.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.
Extended European Search Report for Patent Application No. 06718204.8, May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP 04711207.3.
Extended European Search Report dated Mar. 5, 2012 for European Application No. 12153606.4-1269.
Margare Fyfe et al., Mast cell degranulation and increased vascular permeability induced by therapeutic' ultrasound in the rate ankle joint, Br. J. exp. Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.
Paul Yock et al., Catheter-Based Ultrasound Thrombolysis Shake, Rattle, and Repertuse, https://doi.org/10.1161/01.CIR.95.6.1360 Circulation. 1997;95:1360-1362 Originally published Mar. 18, 1997.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Office Action dated May 20, 2010 from Japanese Application No. 2006-541200 filed on Oct. 25, 2004.
Office Action dated Oct. 11, 2012 from Japanese Application No. 2010-181956.

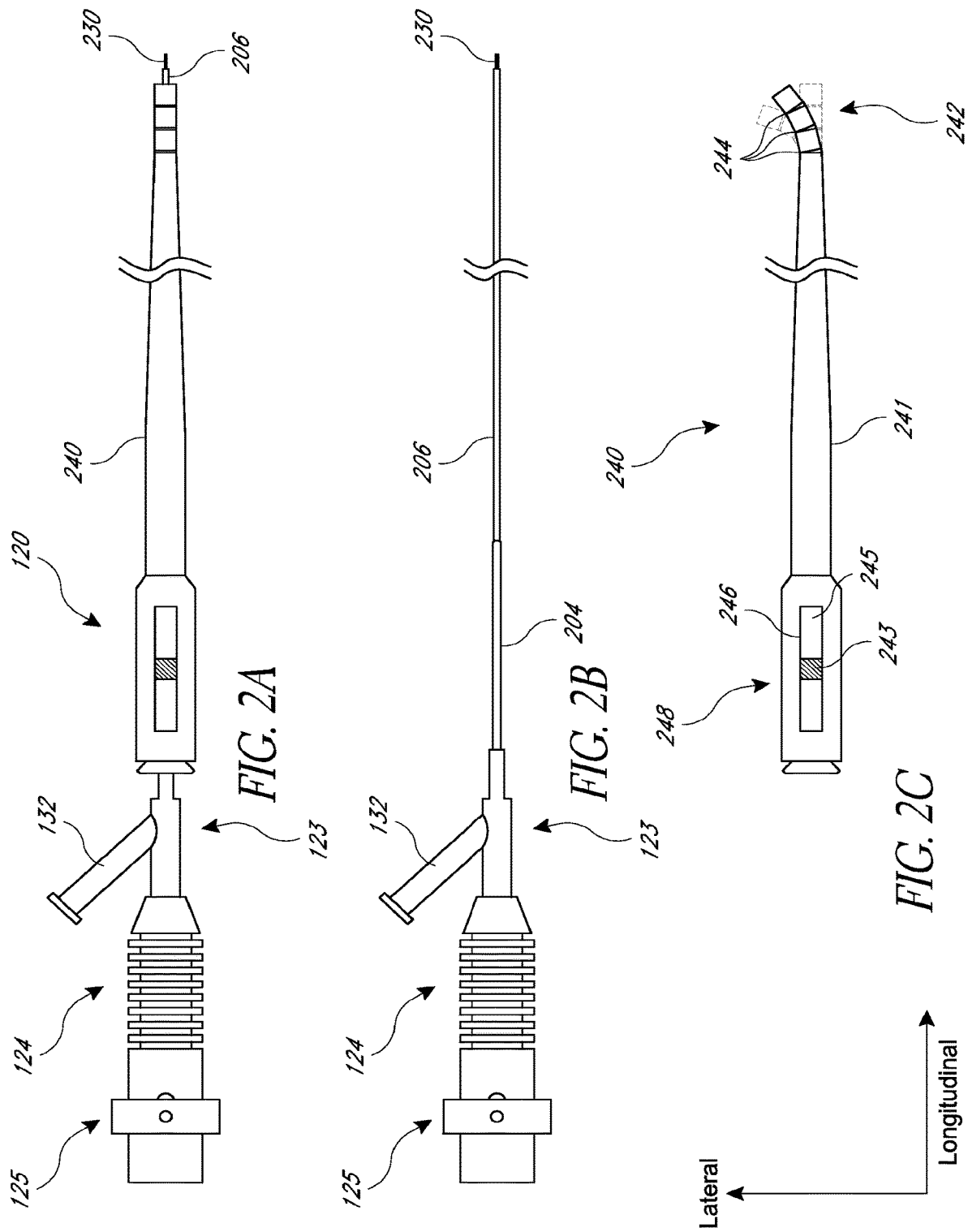

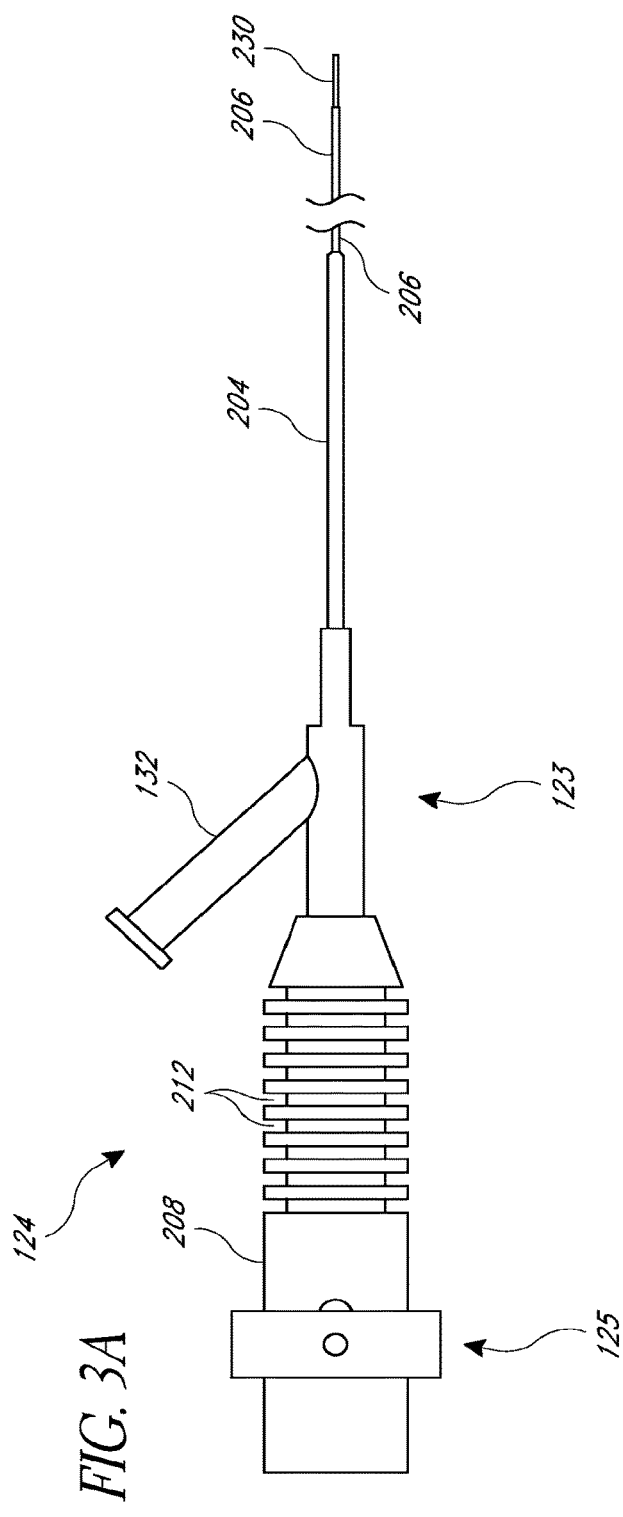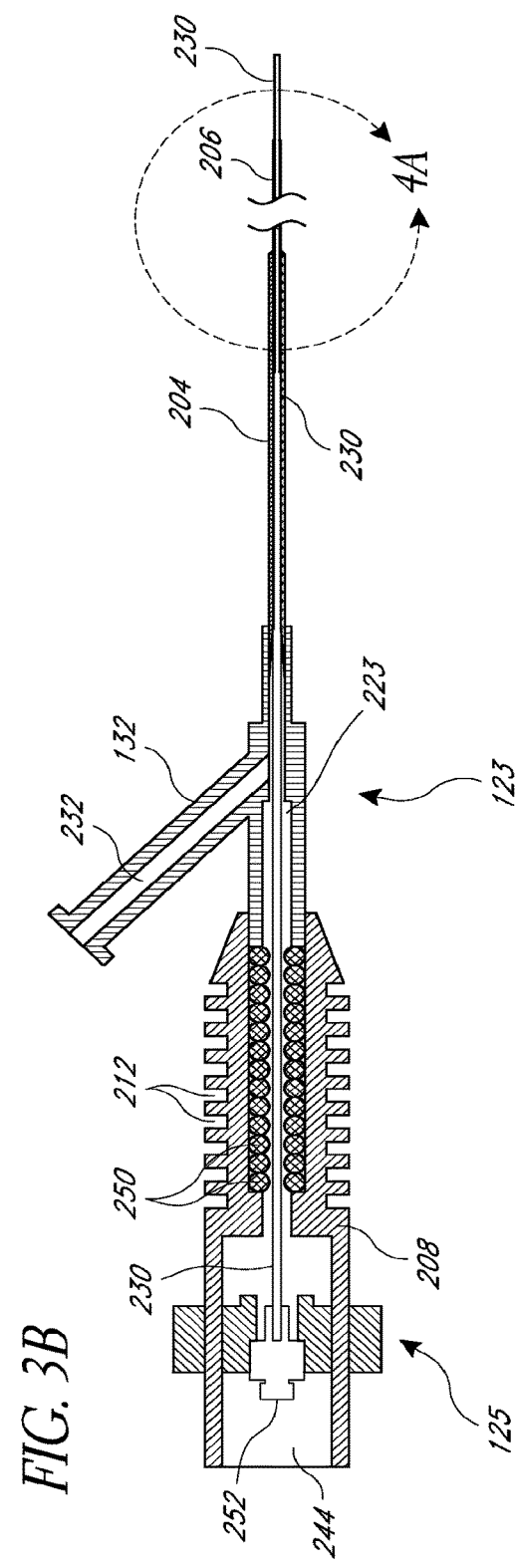

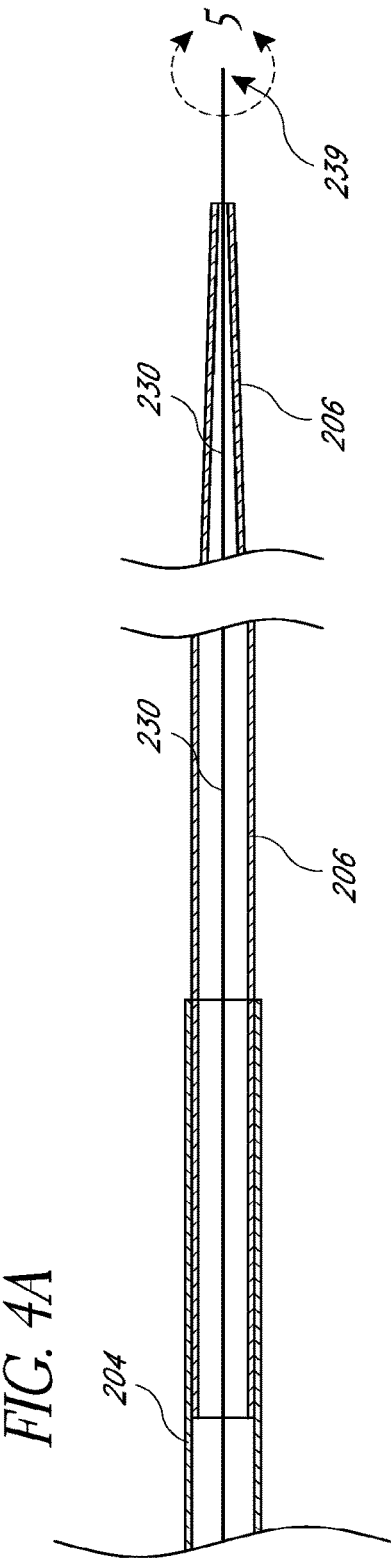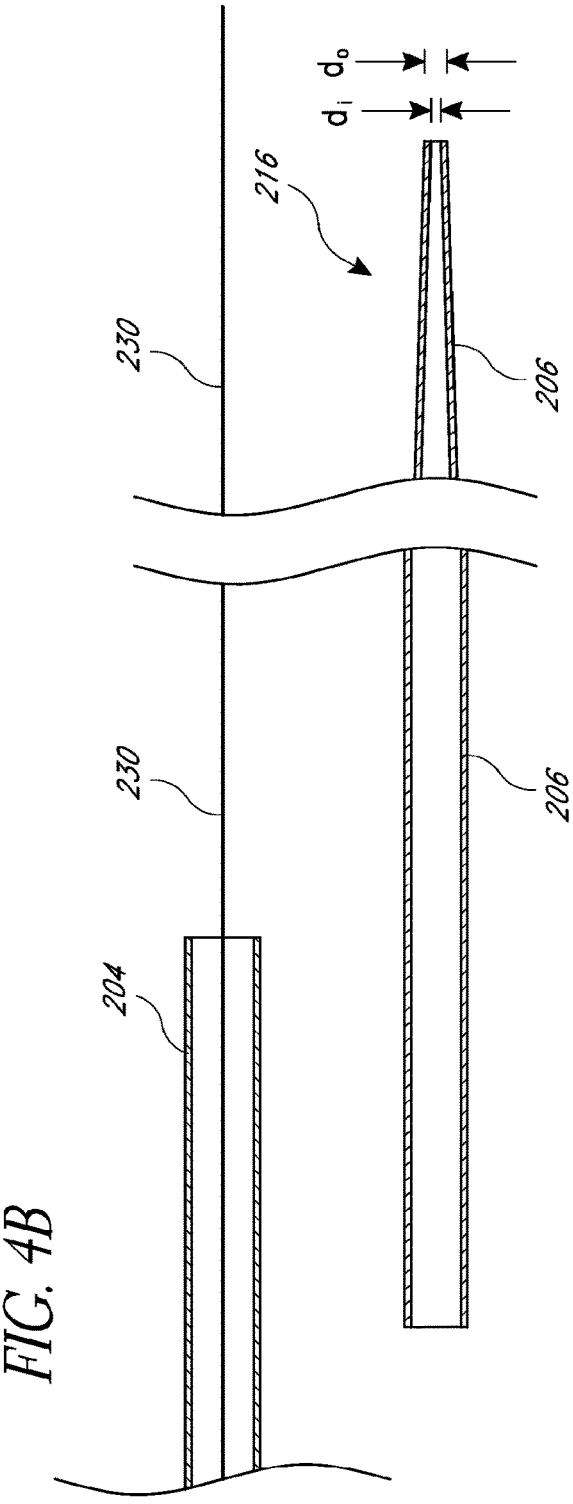
FIG. 4A
FIG. 4B

VASCULAR RE-ENTRY DEVICE

PRIORITY

This application is a continuation of U.S. patent application Ser. No. 15/413,259, filed Jan. 23, 2017, now U.S. Pat. No. 10,357,263, which is a continuation of U.S. patent application Ser. No. 14/365,016, filed Oct. 8, 2014, now U.S. Pat. No. 9,603,615, which is a national stage application under 35 U.S.C. § 371 of International Application No. PCT/US2012/021766, filed Jan. 18, 2012, each of which is incorporated by reference in its entirety into this application.

BACKGROUND OF THE INVENTION

There are many procedures and systems for treating vascular or venous obstructions that are occluded with atheroma, plaque, calcific material, and the like. Such obstructions are often referred to as vascular chronic total occlusions. Total occlusions can be treated, for example, by a surgical bypass procedure or a catheter-based intervention such as angioplasty.

Catheter-based intervention procedures may require the positioning of a guidewire through the occlusion. However, hard occlusive material can be difficult or almost impossible to penetrate. Often, during such procedures, the guidewire deflects from the occlusion and penetrates into an extraluminal space (i.e., subintimal or outside the vessel). The guidewire may even perforate the vessel, resulting in the distal end of the guidewire positioned outside of the vessel wall. Such perforations are very dangerous in certain circulations (e.g., in the brain and the heart). But, perforations are less risky in peripheral arterial circulations and in most of the venous system due to the muscular tissue surrounding these areas. A guidewire positioned in the extraluminal space, between layers of the vessel or outside of the vessel, must be repositioned and/or directed into the central lumen of the vessel. However, redirecting the guidewire is often difficult or impossible, even with the use of ancillary deflecting catheters or devices.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Preferred Embodiments" one will understand how the features of this invention provide several advantages over traditional procedures relating to the treatment of vascular or venous occlusions.

One aspect is an ultrasonic reentry device that includes an elongate ultrasound transmission member that has a proximal end coupled to a sonic connector and a distal end configured to penetrate a vessel wall. The device further includes a catheter body that has a distal end and at least one lumen extending longitudinally therethrough. The lumen surrounds at least a portion of the ultrasound transmission member. The device further includes a dilator removably coupled to the catheter body and surrounding at least a portion of the ultrasound transmission member. The dilator has a length sized to expose at least a portion of the distal end of the ultrasound transmission member when the ultrasound transmission member is disposed within the dilator.

Another aspect is an ultrasonic device for entering and exiting an extraluminal space of a vessel. The device includes a catheter body that has at least one lumen extending longitudinally therethrough and an elongate ultrasound transmission member extending longitudinally through the lumen. At least a portion of the ultrasound transmission member has an outer surface that tapers to a needle-like distal end. The device further includes a dilator disposed over at least a portion of the ultrasound transmission member and configured to follow the ultrasound transmission member into the extraluminal space. At least a portion of the catheter body overlaps at least a portion of the dilator. The device further includes a sheath removably disposed over at least a portion of the dilator.

Another aspect is a method of re-entry from an extraluminal space into a central lumen of a vessel. The method includes positioning an ultrasonic device having a distal end in a first position within the central lumen of the vessel and penetrating the vessel with the distal end of the ultrasonic device. The method further includes advancing the distal end to a second position within the extraluminal space of the vessel and articulating at least a portion of the distal end of the ultrasonic device. The method further includes transmitting a vibration to the distal end of the ultrasonic device and advancing the distal end to a third position different from the first position within the central lumen.

Another aspect is a method of re-entering a central lumen of a vessel from an extraluminal space of the vessel. The method includes advancing a sheath over a guidewire positioned in the extraluminal space of the vessel, removing the guidewire, and advancing an ultrasonic device having a distal end through the sheath. The method further includes articulating at least a portion of the sheath towards the central lumen of the vessel, transmitting a vibration to the distal end of the ultrasonic device, and re-entering the central lumen of the vessel with the distal end of the ultrasonic device.

Another aspect is a system configured to re-enter from an extraluminal space into a central lumen of a vessel. The system can be configured to position an ultrasonic device having a distal end in a first position within the central lumen of the vessel and to penetrate the vessel with the distal end of the ultrasonic device. The system can be further configured to advance the distal end to a second position within the extraluminal space of the vessel and to articulate at least a portion of the distal end of the ultrasonic device. The system can be further configured to transmit a vibration to the distal end of the ultrasonic device and to advance the distal end to a third position different from the first position within the central lumen.

Another aspect is a system configured to re-enter a central lumen of a vessel from an extraluminal space of the vessel. The system can be configured to advance a sheath over a guidewire positioned in the extraluminal space of the vessel, to remove the guidewire, and to advance an ultrasonic device having a distal end through the sheath. The system can be further configured to articulate at least a portion of the sheath towards the central lumen of the vessel, transmit a vibration to the distal end of the ultrasonic device, and re-enter the central lumen of the vessel with the distal end of the ultrasonic device.

BRIEF DESCRIPTION OF THE DRAWINGS

FIG. 2A is a side view of the ultrasound device shown in FIG. 1 coaxially located within a removable sheath.

FIG. 2B is a side view of the ultrasound device shown in FIG. 2A with the sheath removed.

FIG. 2C is a side view of the sheath from FIG. 2A showing an articulating distal end in dashed lines.

FIG. 3A is an enlarged side view of the ultrasound device as shown in FIG. 2B.

FIG. 3B is a cross-sectional view of the ultrasound device as shown in FIG. 3A.

FIG. 4A is an enlarged view of a portion of the ultrasound device about line 4A in FIG. 3B.

FIG. 4B is a view similar to FIG. 4A except the dilator is removed from the catheter body.

DETAILED DESCRIPTION OF CERTAIN PREFERRED EMBODIMENTS

The following description and the accompanying figures describe and show the preferred embodiments as well as demonstrate several possible configurations for a re-entry device, system, and method. The illustrations are not intended to limit the disclosed aspects and features of the invention to the specified embodiments or to usage only with the illustrated device. Those of skill in the art will recognize that the disclosed aspects and features of the invention are not limited to any particular embodiment of a re-entry device, which may include one or more of the inventive aspects and features described herein.

To assist in the description of these components of the re-entry device, the following coordinate terms are used. A "longitudinal axis" is generally parallel to a portion of the re-entry device as well as parallel to the axis of a vessel through which the device can travel. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the re-entry device, and therefore is substantially synonymous with the term "longitudinal" as used herein. Also, the terms "proximal" and "distal," which are used to describe the present system, are used consistently with the description of the exemplary applications (i.e., the illustrative examples of the use applications). Thus, proximal and distal are also used in reference to the respective ends of the re-entry device.

To facilitate a complete understanding of the embodiments, the remainder of the detailed description describes the re-entry system with reference to the Figures; wherein like elements among the embodiments are referenced with like numerals throughout the following description.

Figure 1:
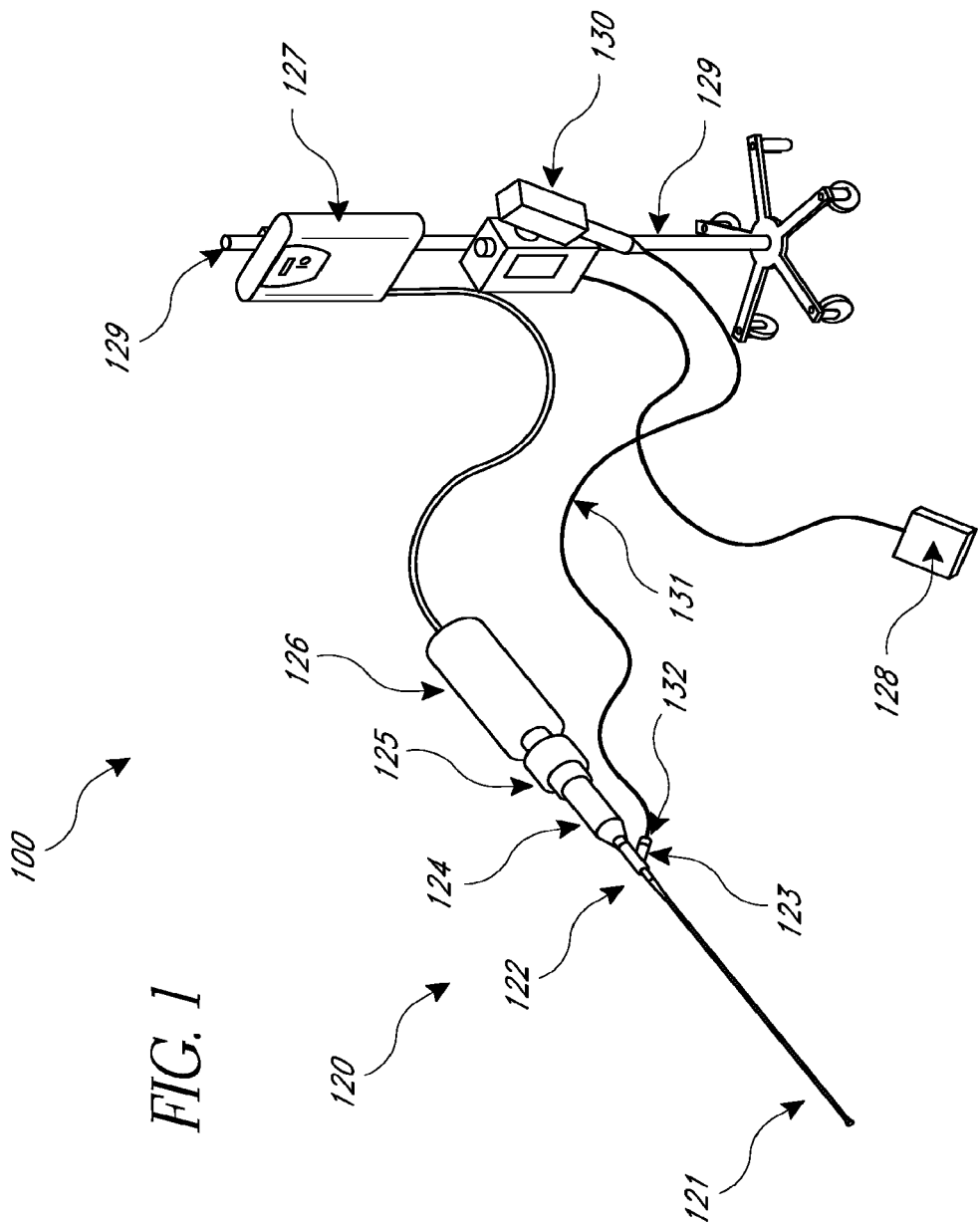
FIG. 1 is a perspective view of an ultrasound system that can be used for vascular re-entry according to a preferred embodiment of the present invention.

FIG. 1 shows an example of a perspective view of an ultrasound system 100 that can be used for vascular re-entry. The ultrasound system 100 includes an ultrasound device 120 which is releasably coupled to an ultrasound transducer 126. The ultrasound transducer 126 is electrically coupled to a signal generator 127.

The ultrasound device 120 may include an elongate body having a proximal portion 122 and a distal portion 121. The ultrasound device 120 may be an ultrasonic energy delivery member, or a catheter having at least one lumen extending longitudinally with an ultrasound transmission member extending therethrough.

The ultrasound device 120 may also include a Y-connector 123 that is operatively coupled to the ultrasound transducer 126. For example, the Y-connector 123 may be coupled to the ultrasound transducer 126 by way of a device knob 124 and a slide collar 125. The ultrasound transducer 126 may be connected to a signal generator 127, which may be coupled to a foot actuated on-off switch 128. The signal generator 127 can be supported by an IV pole 129. When the on-off switch 128 is depressed, the signal generator 127 can send an electrical signal to the ultrasound transducer 126, which converts the electrical signal to ultrasound energy. Such ultrasound energy can subsequently pass through the ultrasound device 120 and be delivered to the distal portion 121. A conventional guidewire (not shown) may be utilized in conjunction with the device 120.

The frontal portion of the Y-connector 123 may be connected to the proximal end 122 of the ultrasound device 120 using techniques that are well-known in the art. An injection pump 130 or IV bag (not shown) or syringe (not shown) may be connected, by way of an infusion tube 131, to an infusion port or sidearm 132 of the Y-connector 123. The injection pump 130 can be used to infuse coolant fluid into and/or through the device 120. Such flow of coolant fluid may be utilized to prevent overheating of the ultrasound transmission member and may serve to bathe the outer surface of the ultrasound transmission member, thereby providing for an equilibration of temperature between the coolant fluid and the ultrasound transmission member. The temperature and/or flow rate of coolant fluid may be adjusted to provide adequate cooling and/or other temperature control of the ultrasound transmission member. The irrigation fluid can include a pharmacological agent and/or microbubbles. In addition to the foregoing, the injection pump 130 or syringe may be utilized to infuse a radiographic contrast medium into the device 120 for purposes of imaging. Examples of iodinated radiographic contrast media which may be selectively infused into the ultrasonic device 120 via the injection pump 130 are commercially available as Angiovist 370 from Berlex Labs, Wayne, N.J. and Hexabrix from Malinkrodt, St. Louis, Mo.

Generally, the ultrasonic device 120 may include any suitable number of side-arms or ports for passage of a guidewire, application of suction, infusing and/or withdrawing irrigation fluid, dye and/or the like, or any other suitable ports or connections. Also, the device may be used with any suitable ultrasound transducer 126, signal generator 127, coupling device(s) and/or the like. Therefore, the exemplary embodiment shown in FIG. 1 and any following descriptions of proximal apparatus or systems for use with ultrasound devices 120 should not be interpreted to limit the scope of the present invention as defined in the appended claims.

FIG. 2A is a side view of the vascular re-entry device shown in FIG. 1 disposed within a removable sheath. The illustrated embodiment of the ultrasound device 120 includes an ultrasound transmission member 230, a dilator 206, and a sheath 240 which together form a tri-axial configuration.

As shown in FIG. 2A, the sheath 240 is removably coupled to the ultrasound device 120. The sheath 240 can be sized and shaped to fit over the catheter body 204, the dilator 206, and the ultrasound transmission member 230. The length of the sheath 240 may be selected such that a portion of the dilator 206 and/or a portion of the ultrasound transmission member 230 remain uncovered by the sheath 204 when the sheath 204 is coupled to the ultrasound device 120.

FIG. 2B is a side view of the ultrasound device 120 shown in FIG. 2A with the sheath 240 removed. As illustrated, the distal portion of the Y-connector 123 is coupled to a catheter body 204. The catheter body 204 can be coupled to the dilator 206. The ultrasound transmission member 230 can pass through the device knob 124, Y-connector 123, catheter body 204, dilator 206, and emerge at the distal end of the ultrasound device 120.

Turning to FIG. 2C, the sheath 240 can be removed from the ultrasound device 120. The sheath 240 may include a proximal handle 248, an actuating distal portion 242, and at least one lumen extending therethrough. The handle 248 may include a mechanism for actuating 246 the distal portion 242. The mechanism 246 may be a member 243 which slides within a channel 245. The member 243 may be coupled to a puller wire (not shown) such that when the member 243 is moved in a longitudinal direction away from the distal portion 242, the puller wire is moved in the same direction causing the distal portion 242 to deflect. In some embodiments, the distal portion 242 deflects up to about 90° from the longitudinal axis. In other embodiments, the distal portion 242 deflects greater than 90°. An advantage of an articulating distal portion 242 over a pre-shaped or curved catheter is the distal portion 242 remains straight when propagating though a vessel and/or extraluminal space, thus reducing trauma to the vessel. Furthermore, the actuating distal portion 242 may allow for added control and accuracy because the amount of deflection can be controlled and/or selected. Sheath 240 may be similar to commercially available sheaths such as, for example, the Bard® Channel™ Steerable Sheath (available from C.R. Bard, Inc., Lowell, Mass.), the CPS Venture® Wire Control Catheter (available from St. Jude Medical, Inc., St. Paul, Minn.), and the Morph® Vascular Access Catheter (available from BioCardia, Inc., San Carlos, Calif.) or other similar such products.

The handle 248 may be coupled with a shaft 241 having at least one lumen extending therethrough. In some embodiments, the shaft 241 is generally tubular in shape and may be constructed to resist snaking when pushed. A stiff shaft construction can prevent snaking when the puller wire is actuated causing the distal portion 242 to deflect. The sheath 240 may be any suitable length, for example, in the range of about 70-150 mm and any suitable diameter, for example, in the range of about 1.5-2.5 mm in order to be positioned though a vascular or venous system.

In some embodiments, the distal portion 242 includes one or more radiopaque markers 244. In one embodiment, the distal portion 242 is made of a radiopaque polymer or similar materials known in the art. The radiopaque materials can increase visibility under fluoroscopy and facilitate the correct positioning of the device. In another embodiment, intravascular ultrasound or other imaging modalities may be employed.

Alternate imaging techniques may include Optical Coherence Tomography (OCT) and/or magnetic fields (Stereotaxis Inc.) to further facilitate orientation of the distal portion 242 towards the central lumen of a vessel and further aid in the re-entry procedure.

FIG. 3A is an enlarged side view of the ultrasound device 120 as shown in FIG. 2B. In the illustrated embodiment, the device knob 124 includes a proximal housing 208. The housing 208 may include one or more surface features 212 for increasing the outer surface area of housing 208. Increased surface area can enhance the ability of housing 208 to dissipate heat generated by ultrasound transmission member 230. Surface features 212 may be of any suitable size or shape and can include, for example, ridges, jags, undulations, grooves or the like. Any suitable number of surface features 212 may be used. Additionally, the housing 208 may be made of one or more heat dissipating materials, such as aluminum, stainless steel, any other conductive metal(s), or any suitable non-metallic conductive material.

The catheter body 204 may be a generally flexible, tubular, elongate member, having any suitable diameter and length for reaching a vascular occlusion. Some embodiments, for example, the catheter body 204 has a length in the range of about 100200 cm. In one embodiment, the catheter body 204 has an outer diameter in the range of about 0.5-5.0 mm. In other embodiments, for use in relatively small vessels for example, the catheter body 204 may have an outer diameter in the range of about 0.25-2.5 mm. However, any other suitable length or diameter may be used without departing from the scope of the present invention. Examples of catheter bodies similar to those which may be used in the present invention are described in U.S. Pat. Nos. 5,267,954 and 5,989,208, which are herein incorporated by reference in their entireties. The catheter body 204 can insulate the ultrasound transmission member 230 and prevent an operator's hands from contacting the ultrasound transmission member 230 during use of the device.

FIG. 3B shows a cross-sectional view of the ultrasound device 120. As depicted, the housing 208 can include an inner cavity 244. Disposed within the cavity 244 is a sonic connector 252. The ultrasound transmission member 230 extends in a distal direction from the sonic connector 252 and through the cavity 244.

The inner cavity 244 may include one or more vibration absorption members 250. The vibration absorption members 250 can increase the ease of use by decreasing vibrations transmitted from the ultrasound transmission member 230 through the housing 208. The sonic connector 252 can facilitate the coupling of the ultrasound transmission member 230 to an ultrasound transducer device 126. The ultrasound transmission member 230 may extend distally from the sonic connector 252, through the inner cavity 244, Y-connector 216, catheter body 204, and dilator 206.

Continuing with FIG. 3B, the sidearm 132 may include a lumen 232 in fluid communication with a lumen 223 in the Y-connector 123. The lumen 223 in the Y-connector 123 can be in fluid communication with a lumen extending through the catheter body 204. Thus, fluid introduced into the sidearm 132 may flow into and through the catheter body 204 and contact the ultrasound transmission member 230. The fluid may flow out of the catheter body 204 through apertures in the distal portions (not shown) or through any other suitable apertures or openings, such as apertures located in the catheter body 204 itself.

Any suitable fluid may be passed through the sidearm 132 and catheter body 204. Suitable fluids include, for example, refrigerated fluids, lubricious fluids, super-saturated saline or contrast/saline mixtures, or the like. Cooling and/or lubricating the ultrasound transmission member 230 may reduce friction and/or wear and tear of the ultrasound transmission member 230, thus prolonging the ultrasound transmission member's useful life and enhancing overall performance.

In some embodiments, the ultrasound transmission member 230, wire, or wave guide extends longitudinally through a lumen of the catheter body 204. Ultrasonic energy can travel through the ultrasound transmission member 230 from an ultrasound transducer 126 connected to the proximal end of housing 208 to the distal portion of the device. The ultrasound transmission member 230 may operate at frequencies between about 10 Hz to about 20 MHz. In one embodiment, the frequency of vibration is 20 kHz. The ultrasound transmission member 230 may operate in continuous mode, pulse mode, or combination of both.

The ultrasound transmission member 230 may be formed of any material capable of effectively transmitting ultrasonic energy from the ultrasound transducer to the distal end of the ultrasound transmission member 230. These materials include, but are not limited to, metals such as pure titanium or aluminum, or titanium or aluminum alloys, such as NiTi. The ultrasound transmission member 230 may include one or more tapered regions and/or steps. The tapered regions and steps may increase and/or decrease in width or diameter along the length of the ultrasound transmission member 230 in the distal direction. In one embodiment, the ultrasound transmission member 230 includes at least one portion tapered in a direction extending distally from the proximal end. In another embodiment, the ultrasound transmission member 230 is continuously tapered in a direction extending distally from the proximal end. In one embodiment, the ultrasound transmission member 230 tapers in diameter from about 800 pm proximally, to about 200 pm distally.

Additional details of ultrasound systems and devices that include ultrasound transmission members (and their distal tips), ultra-sound transducers, sonic connectors and their connections to ultrasound devices are disclosed in U.S. Pat. Nos. 6,007,514, 6,427,118; 6,702,748; 6,855,123; 6,942,620; 6,942,677; 7,137,963; 7,220,233; 7,297,131; 7,335,180; 7,393,338; 7,540,852, 7,604,608 and in U.S. Pat. Pub. Nos. 2008/0108937, 2008/0287804, 2010/0317973, the disclosures of which are hereby incorporated by reference in their entireties.

Continuing with FIG. 3B, the Y-connector 123 can be coupled to the catheter body 204. The catheter body 204 can be coupled to the removable dilator 206. The Y-connector 123 can be coupled to the catheter body 204 by any coupling manner well known in the art and in some embodiments is fixably attached. Similarly, the removable dilator 206 can be coupled to the catheter body 204 in any manner well known in the art. In some embodiments, a separate coupling structure is used.

In some embodiments, as shown for example in FIGS. 4A and 4B, the removable dilator 206 is coupled to the catheter body 204 such that the catheter body 204 overlaps at least a portion of the dilator 206. As illustrated, a proximal portion of the dilator 206 is sized to fit within a distal portion of the catheter body 204. In other words, the dilator 206 can be placed around the ultrasound transmission member 230 and fit within the catheter body 208.

In some embodiments, an outer surface of the dilator 206 contacts an inner surface of the catheter body 204. Friction between the two surfaces can secure the dilator 206 in place. The length of the dilator 206 may be selected so that at least a portion of the ultrasound transmission member 230 is exposed at the distal end. The total length of the dilator 206 can be selected, for example, such that about 5 mm of the distal portion of the ultrasound transmission member 230 is exposed when a proximal portion of the dilator 206 is fit snugly within the distal portion of the catheter body 204.

The dilator 206 may be a thin walled tubular member and constructed such that the dilator 206 is resistant to bending or kinking when pushed. The dilator 206 may be formed with any suitable material well known in the art, including but not limited to flat-ribbon braided polyamide, or may comprise a hypotube catheter shaft of stainless steel, titanium, NiTi, or similar metal/alloy. In one embodiment, at least a portion of the dilator 206 is tapered in a direction extending distally from the proximal end. In another embodiment, the dilator 206 is continuously tapered in a direction extending distally from the proximal end.

Turning to FIG. 4B, a distal portion of the dilator 206 may have a similar profile to the ultrasound transmission member 230 such that the distal portion of the dilator 206 is sized to facilitate the following of the ultrasound transmission member 230 into the extraluminal space. In use, the dilator 206 can serve as a transition member between the relatively small diameter of the ultrasound transmission member 230 and the relatively larger diameter of the sheath 240. For example, the dilator 206 can follow the ultrasound transmission member 230 into the extraluminal space and the sheath 240 can then follow the dilator 206 into the extraluminal space as well. In one embodiment, the distal portion of the dilator 206 has an inner diameter $d_i$ and outer diameter $d_o$ in the range of about 500-250 pm. In one embodiment, the inner diameter $d_i$ is about 380 pm and the outer diameter $d_o$ is about 480 pm.

Figure 5B:
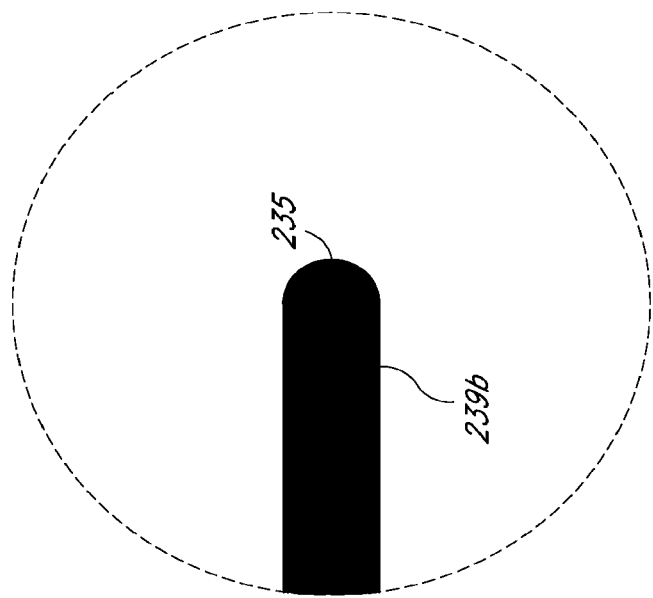
FIG. 5B is an enlarged view of another embodiment of the distal end of the ultrasound device about line 5 in FIG. 4A.
Figure 5A:
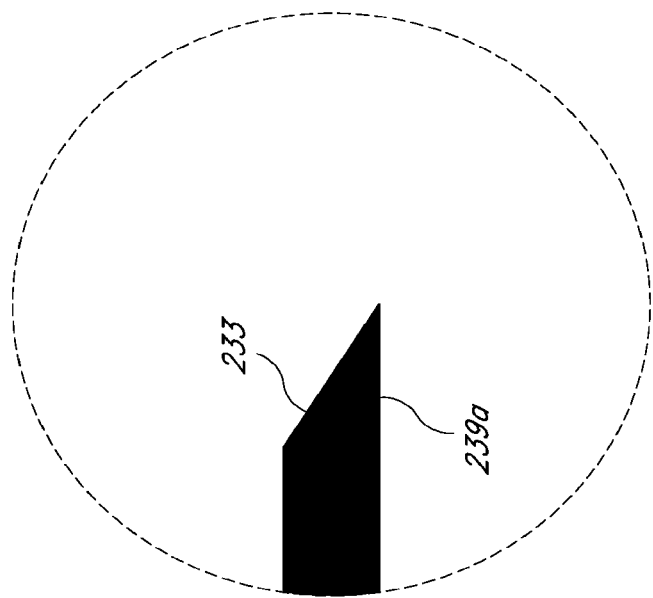
FIG. 5A is an enlarged view of an embodiment of a distal end of the ultrasound device about line 5 in FIG. 4A.

FIGS. 5A and 5B show enlarged side views of exemplary embodiments of the distal tip 239 of the ultrasound transmission member 230. In some embodiments, the distal tip 239 is integral to the ultrasound transmission member 230 and is not formed by a separate tip structure or component attached to the ultrasound transmission member 230. Rather, in these embodiments, the distal tip 239 is formed by shaping the distal end of the ultrasound transmission member 230. A sharpened distal end facilitates penetration into blood vessel materials. The lack of an affixed tip structure which often includes a larger diameter allows for greater power intensity to be transmitted to the distal tip 239 of ultrasound transmission member 230. FIG. 5A shows a distal tip 239a with a chiseled end, having a beveled edge 233. FIG. 5A shows a distal tip 239b with a rounded edge 235. Other similar constructions may also be implemented. For example, in one embodiment, the distal tip of ultrasound transmission member 239 has a conical shape.

A Total Occlusion ("TO") can be defined as an artery or vein that has been completely occluded. An acute TO is usually associated with a sudden blockage, resulting in no blood flow to and from surrounding tissue, and is potentially life threatening. In contrast, Chronic Total Occlusions ("CTO") are blockages that have formed for at least thirty days and are less life-threatening. In such cases, the areas around the CTO tend to develop collateral blood supply.

Figure 6:
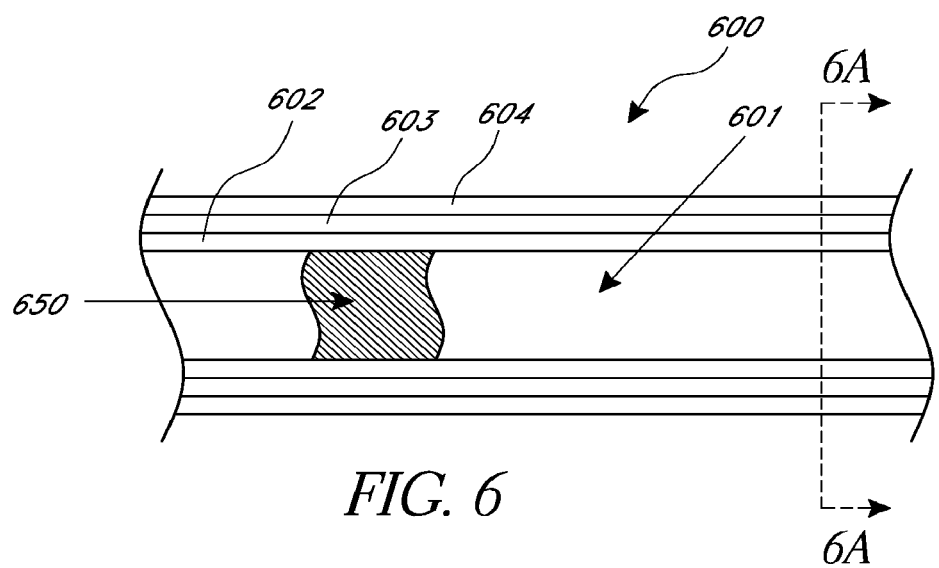
FIG. 6 shows a longitudinal cross-sectional view of an artery having a total occlusion (TO) or chronic total occlusion (CTO).

FIG. 6 illustrates a longitudinal cross-sectional view of an artery 600 having a total occlusion 650. The total occlusion 650 usually consists of atheroma, thrombus, plaque, calcific material, or combinations of thereof. For illustrative purposes, an arterial CTO 650 is shown in connection with the device and method described with respect to FIGS. 7-13.

However, all the devices and methods described herein can also apply to CTOs within veins. Further, although the ultrasonic device will be shown and described for use in and about an artery, the device may also be used in other blood vessels including veins and capillaries or in other tubular channels, for example channels of the lymphatic system. As illustrated in FIG. 6, the arterial occlusion 650 occupies the entire diameter of the lumen, thus blocking blood flow. It is desirable to open such an occlusion, restoring blood flow through affected areas, and thus improving blood supply and heart function.

Figure 6A:
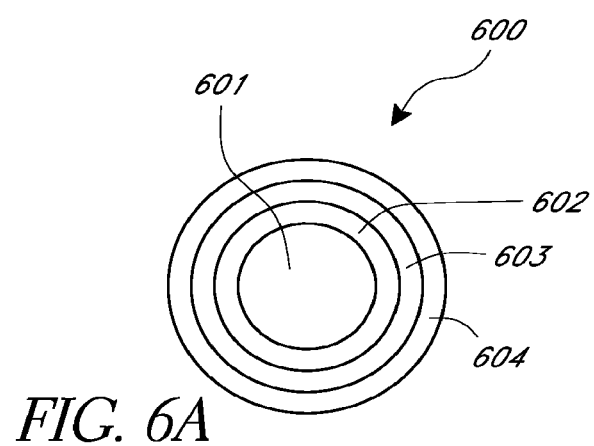
FIG. 6A shows a lateral cross-sectional view through the artery of FIG. 6 taken at line 6A-6A.

FIG. 6A illustrates a cross section of the artery 600 about the line 6A-6A as viewed in a direction distal to the occlusion. The artery has a central lumen 601 and arterial wall with three layers: intima 602, intermedia 603 and adventitia 604. All three layers consist of elastic tissue, smooth muscle and connecting tissue (collagen). The tissue of the arterial wall is often called a subintimal space. The area outside the adventitia 604, an external layer of the artery, is called a space outside of the vessel. Both areas, subintimal space and outside the vessel space, are referred to collectively herein as "extraluminal space."

Figure 7:
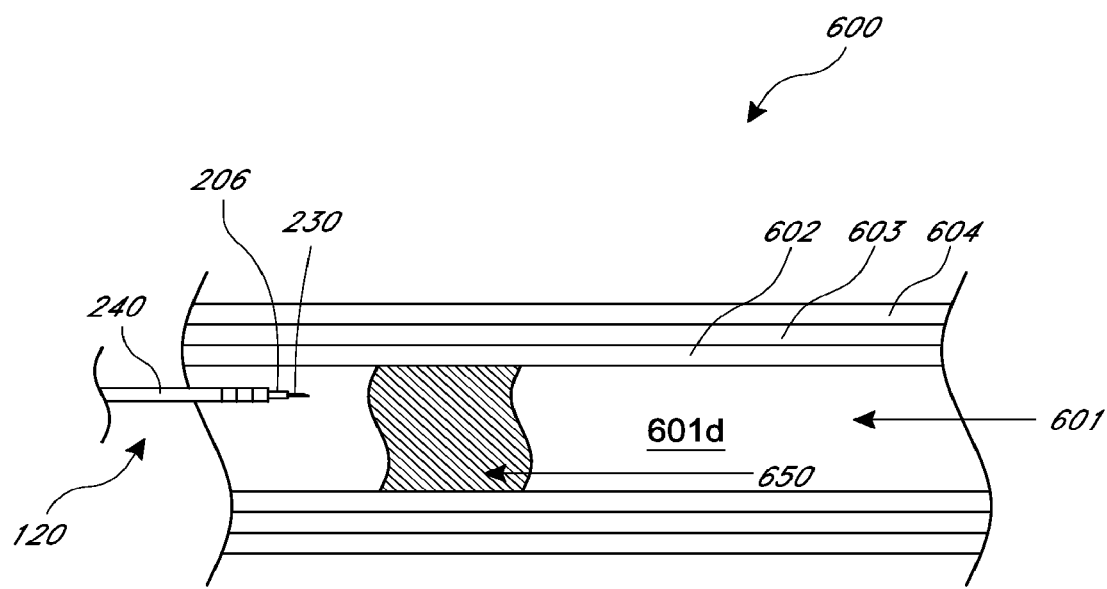
FIGS. 7-13 show an exemplary series of steps to bypass the CTO using the ultrasound device disclosed herein.

FIGS. 7-13 illustrate the steps of an exemplary use of the ultrasonic device 120 in a vascular re-entry procedure. As shown in FIG. 7 the ultrasonic device 120 can be positioned in the vessel 600 and advanced until the device 120 encounters the occlusion 650. In the illustrated embodiment, the ultrasonic device 120 includes an ultrasound transmission member 230 disposed within a dilator 206. The dilator 206 and ultrasound transmission member 230 are further disposed within the sheath 240. The sheath 240 includes an articulating distal portion.

Figure 8:
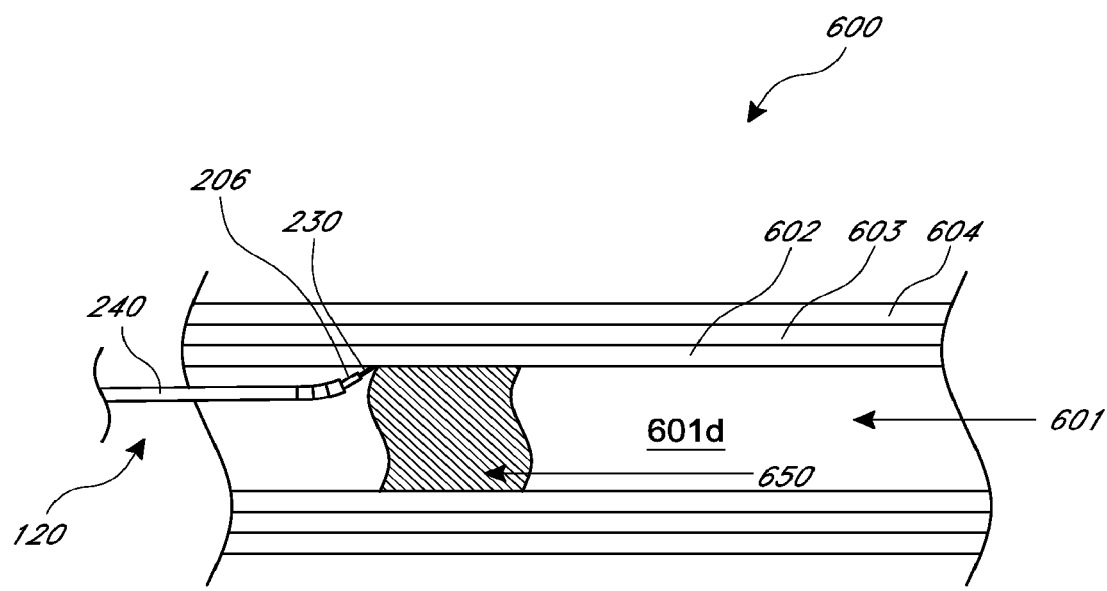

Sometimes, the ultrasonic device 120 can be successfully advanced through the occlusion 650 and positioned in the central lumen 601d of the vessel 600, distal to the occlusion. However, as shown in FIG. 8, the ultrasonic device 120 may deflect away from the occlusion 650 and toward the wall of the vessel. In FIG. 8, the ultrasonic device 120 is shown as deflecting laterally, towards the vessel wall.

Figure 9:
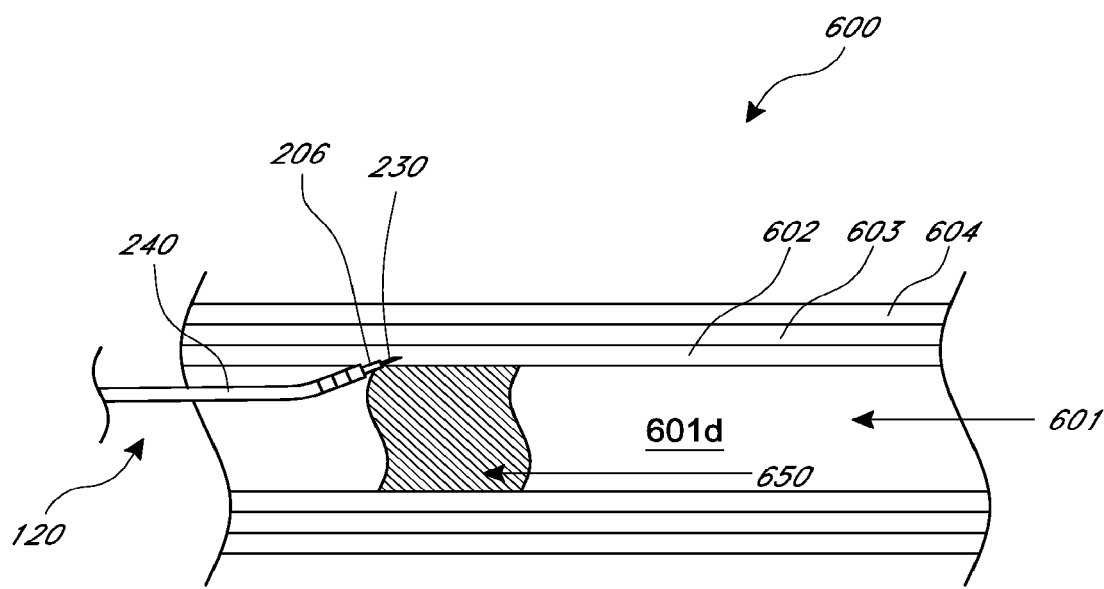

With reference to FIG. 9, the ultrasonic device 120 is advanced further so as to penetrate the intima layer 602 of the vessel 600. A sharp tipped 239 ultrasound transmission member 230 can allow for easier penetration into the intima layer 602. As the ultrasonic device 120 is advanced further, the low-profile dilator 206 follows the ultrasound transmission member 230 into the intima layer 602 as well.

Figure 10:
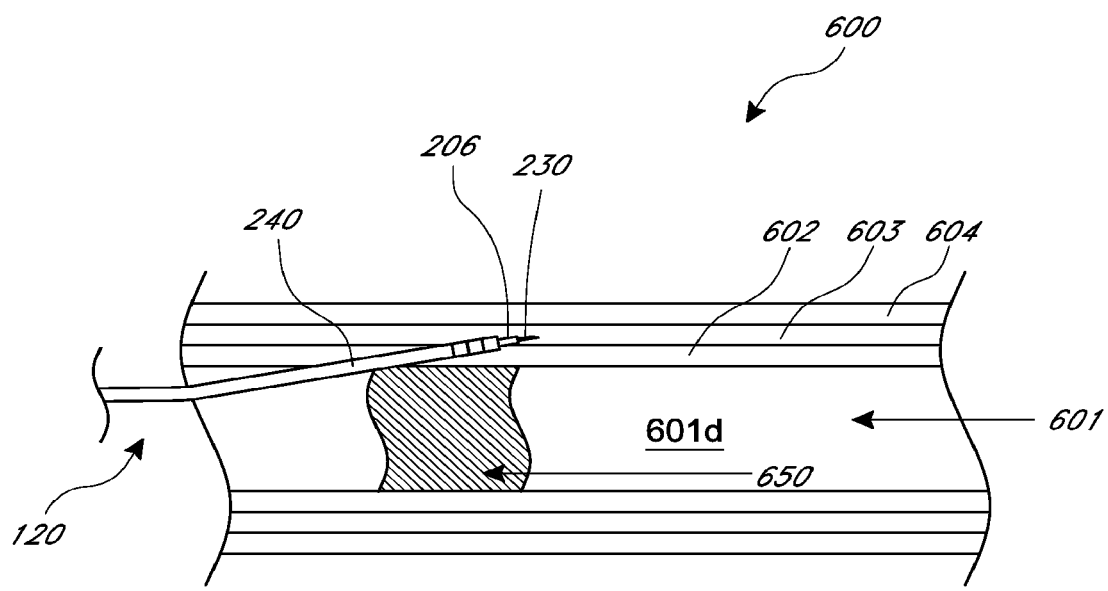

Continuing to FIG. 10, the ultrasonic device 120 is advanced further within the extraluminal space of the vessel 600. As illustrated, the sheath 240 follows the dilator 206 into the intima layer 602 such that the distal portion of the ultrasonic device 120 is positioned between the intima layer 602 and the intermedia layer 603. The ultrasonic device 120 may also be advanced into the adventitia 604 layer or even to areas outside the vessel 600. In one embodiment, the ultrasonic device 120 is advanced within the subintimal space until it passes the occlusion 650.

Vessel trauma can be minimized if the distance that the ultrasonic device 120 travels through the subintimal space is minimized. Thus, it is desirable that the path length of the ultrasonic device 120 through the subintimal space is as short as possible. In some embodiments, the ultrasonic device 120 is advanced to just beyond the proximal end of the occlusion 650. Often, when occlusions are long and there is evidence of softer occlusion composition, the proximal advancement of the ultrasonic device 120 should be limited as much as possible. Thus, if possible, re-entry within the occlusion 650 should be considered as well to minimize the length of the subintimal space in which the ultrasonic device 120 will occupy.

With other similar devices, re-entry from the subintimal or extraluminal space into the central distal lumen 601d may be difficult. For example, a conventional guidewire may be unable to re-enter into the distal central lumen 601d due to the muscular vessel structure which may prevent the relative soft guidewire from puncturing the vessel wall. A directing catheter disposed over the guidewire may also not provide sufficient support for the guidewire to puncture the vessel wall. Traditional directing catheters are often pre-shaped, causing added damage to the vessel wall.

Figure 11:
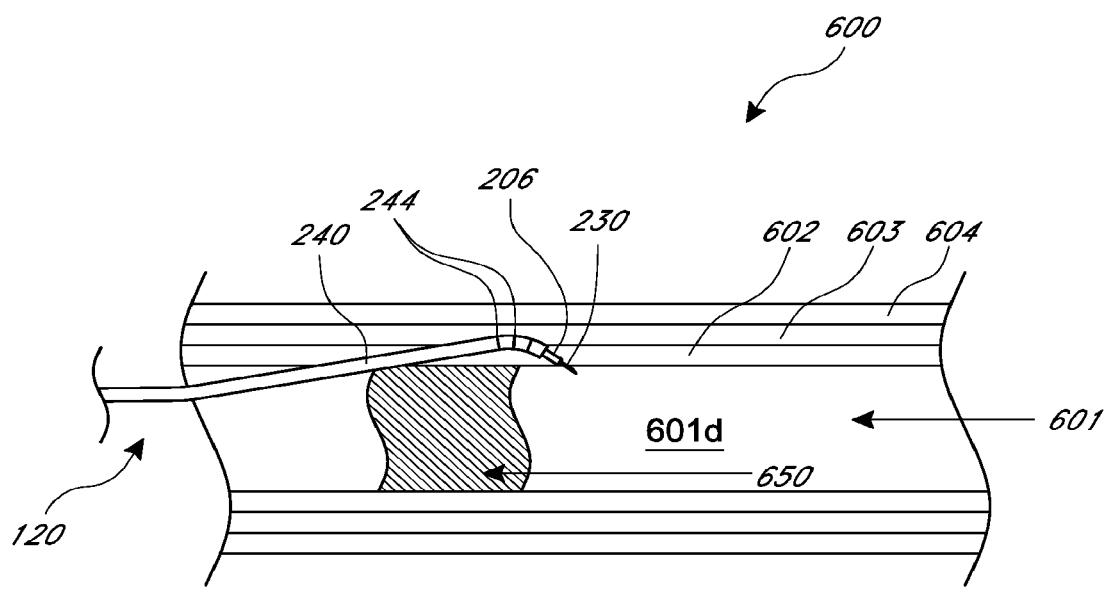

FIG. 11 shows a distal portion of the ultrasonic device 120 positioned within the subintimal space beyond the occlusion 650. In one embodiment, the position of the sheath 240 is determined at least in part by visualizing the radiopaque markers 244 with fluoroscopy techniques. The ultrasonic device 120 can be rotated and/or advanced as desired based at least in part on the known location of the radiopaque markers 244. Once the ultrasonic device 120 is placed in a desired position, the sheath 240 can be actuated such that the distal portion of the sheath 240 deflects in a direction towards the distal central lumen 601d. The precise amount of deflection can be selected and/or varied during the procedure by the device operator.

In order to determine the precise position and orientation of the ultrasonic device 120, extensive flouroscopical visualization from several X-ray machine angles may be required. Such visualization may be needed during positioning to assure that the distal portion of the device is directed towards the distal central lumen 601d. Use of endovascular ultrasound or other visualization devices, either in arteries or in adjacent veins, may also facilitate directing the distal portion of the ultrasonic device 120 towards the distal central lumen 601d.

According to one embodiment, when it is confirmed that the distal portion of the ultrasonic device 120 is directed towards the distal central lumen 601d, ultrasonic energy is transmitted to the distal portion of the ultrasound transmission member 230. The ultrasonic device 120 is then slowly advanced through the subintimal space to puncture the vessel wall. The ultrasonic device 120 can then be advanced into the distal central lumen 601d. The delivery of ultrasonic energy may then be reduced or stopped.

Ultrasonic energy, with its cavitational and/or thermal effects, may be helpful in ablating or penetrating, perforating, or piercing the vessel 600 and facilitate reentry into the distal central lumen 601d. Vibrational devices with longitudinal or transverse vibrational forces, rotational devices, or other heat generating devices such as radio frequency or microwave devices may be used to facilitate re-entry into the distal central lumen 601d. As such, in other embodiments, the ultrasonic device 120 may include other vibrational devices, rotational devices, cutting devices, radio frequency devices, laser devices, microwave devices, puncture devices, and the like.

Figure 12:
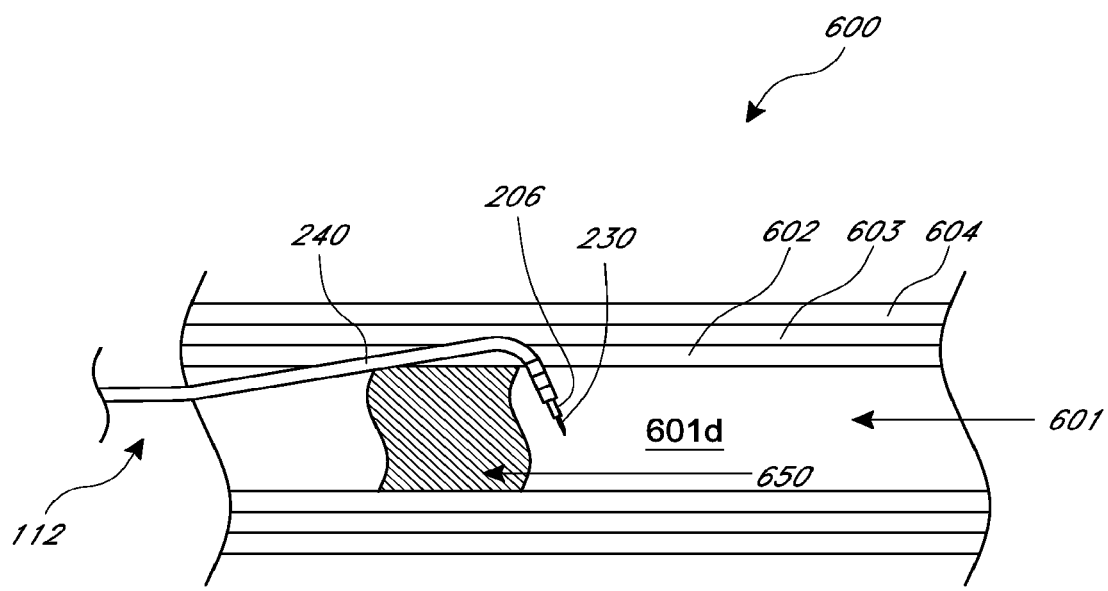

FIG. 12 illustrates a distal portion of the ultrasonic device 120 positioned in the distal central lumen 601d beyond the occlusion 650. In some embodiments, the portion of the ultrasound transmission member 230 exposed (i.e. not covered by the dilator 240 and/or sheath 206) is minimized in order to reduce the potential for piercing the opposite wall of the vessel 600.

Figure 13:
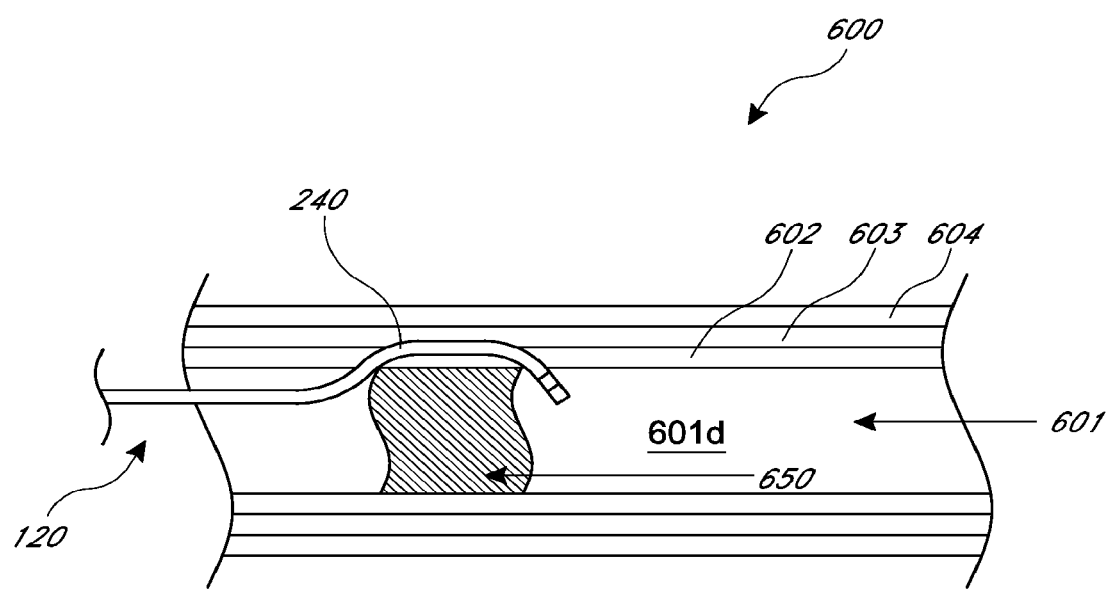

In the embodiment shown in FIG. 13, once at least a portion of the sheath 240 is positioned distal to the occlusion 650 and within the distal central lumen 601d, the ultrasound transmission member 230 and the dilator 206 can be removed from the sheath 240. An adjunctive angioplasty such as balloon angioplasty and/or stenting can then be inserted into the sheath 240. The sheath 240 can then be removed and the adjunctive angioplasty can be deployed, completing the procedure according to one embodiment.

Figure 14:
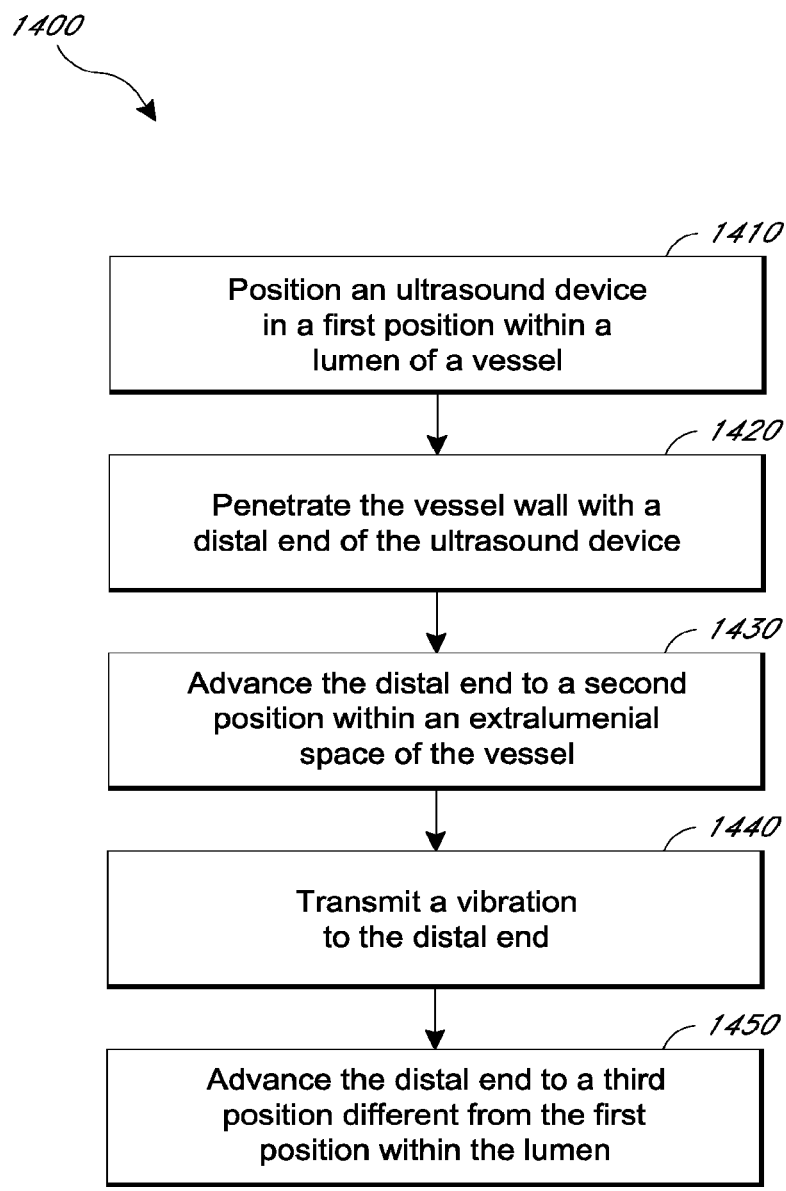
FIG. 14 is a flow diagram illustrating a method of bypassing the CTO by re-entering the artery from an extraluminal space.

FIG. 14 is a flow diagram illustrating a method of re-entry from an extraluminal space into a lumen of a vessel. The method 1400 begins at block 1410 by positioning an ultrasound device 120 in a first position within a lumen of a vessel. The first position may be proximal to a vessel blockage. The method continues at block 1420 by penetrating the vessel wall with a distal end of the ultrasound device 120. At least a portion of the distal end preferably articulates or bends. In some embodiments, the ultrasound transmission member includes a sharpened distal end configured to facilitate the ultrasound device 120 penetrating the vessel wall. The method continues at block 1430 by advancing the distal end of the ultrasound device to a second position. The second position may be within an extraluminal space of the vessel, for example, in a space outside of the lumen of the vessel, or within the vessel wall. In some embodiments, at least a portion of the distal end is articulated to bend in a direction towards or away from the vessel wall.

The method 1400 continues at block 1440 by transmitting a vibration to the distal end. The vibration may be in the form of an ultrasonic vibration transmitted from a proximal end of the ultrasonic device to the distal end. The method 1400 can end at block 1450 by advancing the distal end to a third position different from the first position within the lumen. The third position may be at a position distal to the vessel blockage. The ultrasound device 120 may include an outer lumen surrounding an ultrasound transmission member 230. In some embodiments the method continues by removing the ultrasound transmission member 230 from the lumen and replacing it with a scent or balloon catheter or the like.

FIGS. 15-25 show another exemplary series of steps to repair an initially unsuccessful bypass procedure using the ultrasound device 120 disclosed herein. As discussed above, an occluded vessel can be treated at least in part by positioning a guidewire through the occlusion. For some methods of bypassing an occlusion or CTO, the procedure initially begins with the medical provider feeding a conventional guidewire through the vasculature and adjacent to the CTO. The medical provider may then press the guidewire firmly against the CTO in an attempt to penetrate the CTO unaided by the ultrasound device 120. In such cases, the guidewire may successfully penetrate the CTO or be deflected away from the CTO and into the wall of the vessel. In some cases the deflected guidewire punctures the vessel wall and enters the subintimal space. As set forth below, one of the many medical uses for the ultrasound device 120 is to reposition such a guidewire back within the true lumen of the vessel.

Figure 15:
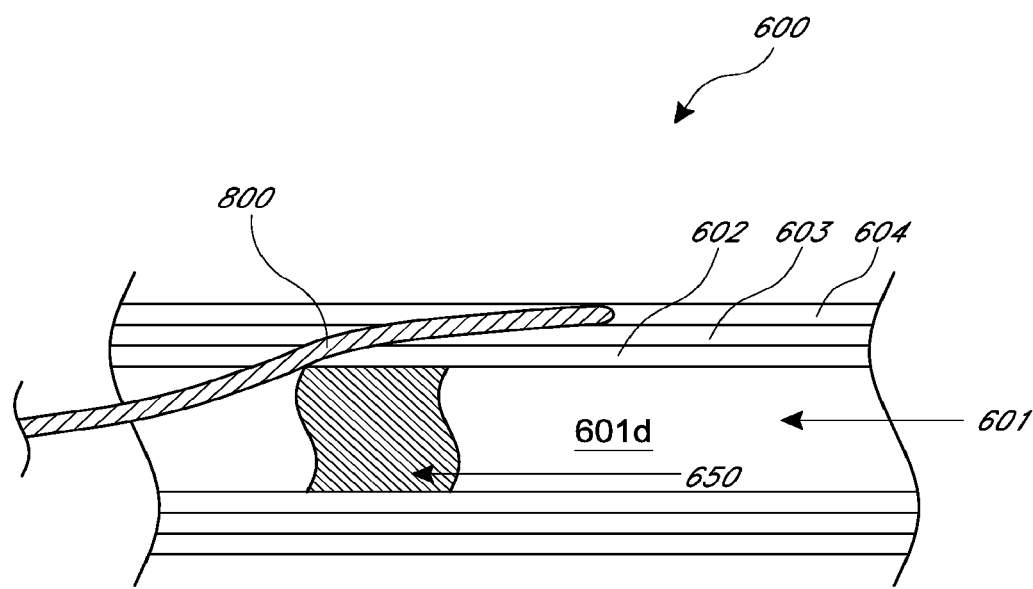
FIGS. 15-25 show another exemplary series of steps to repair an unsuccessful bypass procedure by repositioning a conventional guidewire using the ultrasound device disclosed herein.

FIG. 15 illustrates a traditional guidewire 800 that has deflected away from an occlusion 650, toward the wall of the vessel, and into the subintimal space. The tri-axial ultrasound device 120 can be used in a method to reposition the guidewire 800 in a desired position as described below.

Figure 16:
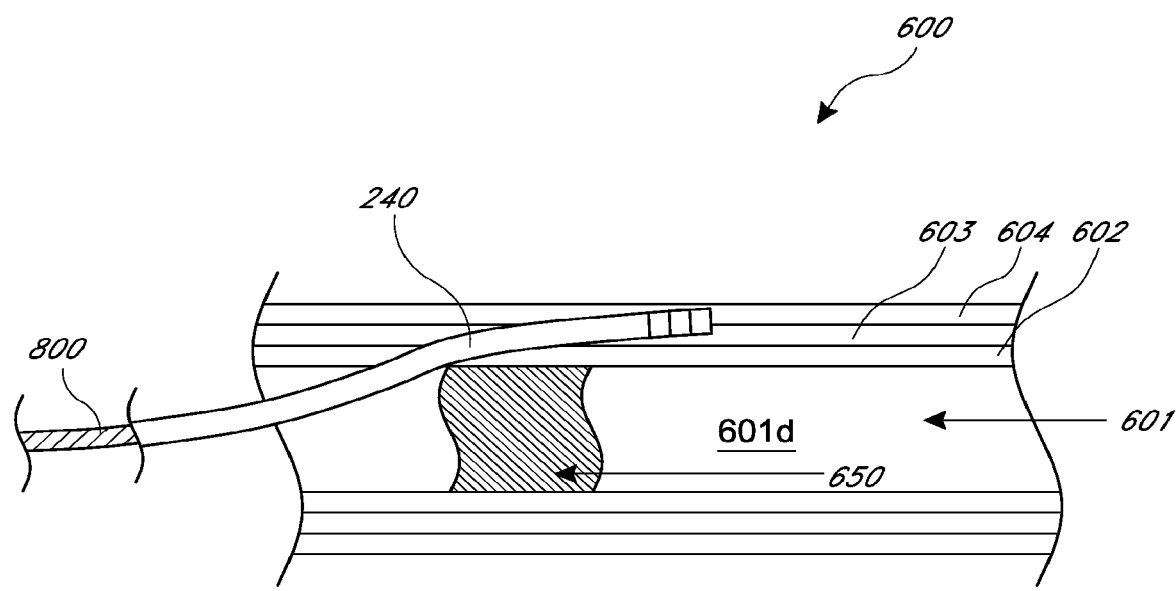

In some embodiments, the bailout method begins as is illustrated in FIG. 16 with a sheath 240 being advanced over the guidewire 800 and into the subintimal space of the vessel. The sheath 240 may include radiopaque markers 244 to help determine the precise position and orientation of the sheath 240. The sheath 240 can include an articulating distal end as discussed above.

Figure 17:
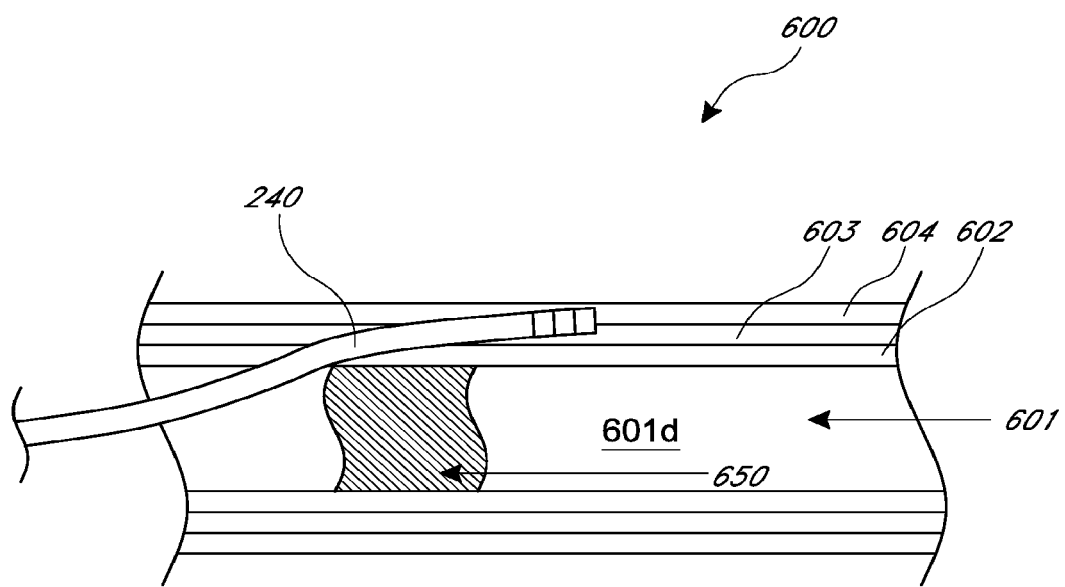

The method continues in FIG. 17 by removing the guidewire 800 from the sheath after the sheath 240 has been advanced over the guidewire 800. In this way, at least a portion of the sheath 240 remains at least partially within the subintimal space. The positioning of the sheath 240 can be determined, for example, by visualizing the radiopaque markers 244.

Figure 18:
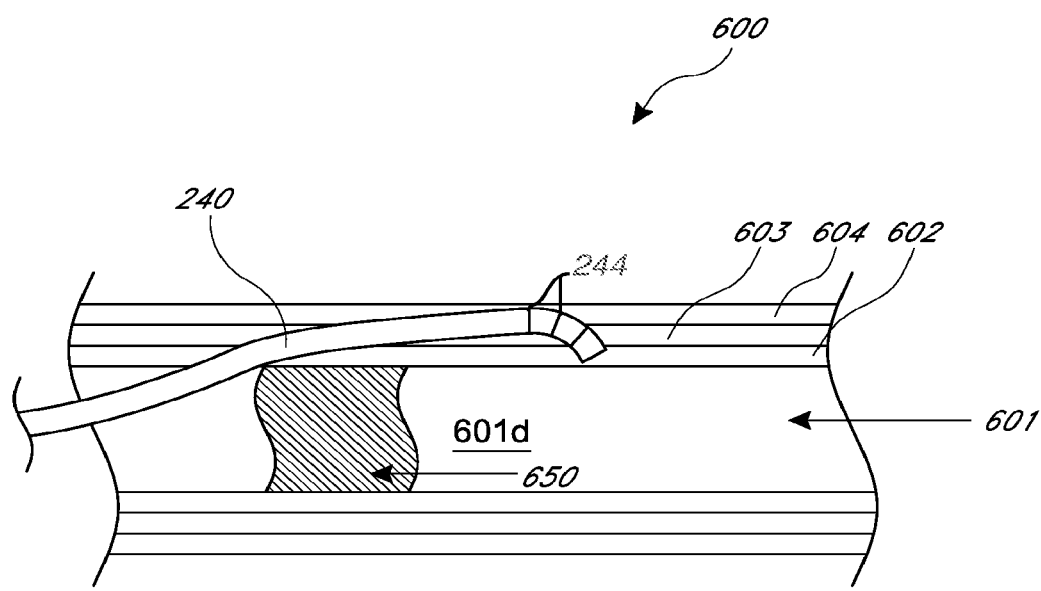

The articulating distal end of the sheath 240 can then be actuated such that a distal portion of the sheath 240 deflects in a direction toward the distal central lumen 601d of the vessel as shown in FIG. 18. FIG. 18 illustrates an embodiment in which the sheath 240 is articulated with the guidewire 800 removed. However, the sheath 240 can be articulated before the guidewire 800 is removed as well. The sheath 240 can also be articulated before or after other devices or lumens have been inserted into the sheath 240.

Figure 19:
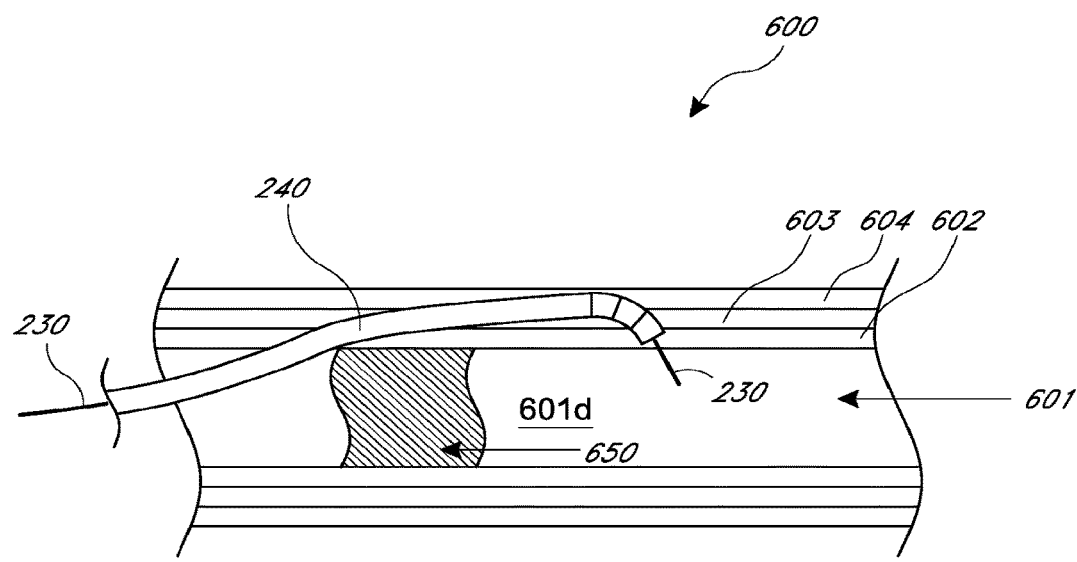

The next step of the method is illustrated in FIG. 19. An ultrasound transmission member 230 is advanced through the sheath 240. The ultrasound transmission member 230 may include a distal tip configured to penetrate tissue. The ultrasound transmission member 230 may be connected to a source of ultrasonic energy and configured such that ultrasonic vibrations can be transmitted to the tip of the ultrasound transmission member 230 to facilitate penetration of the vessel wall and/or to assist in re-entry from the subintimal space and into the distal central lumen 601d. As shown in FIG. 19, a distal portion of the ultrasound transmission member 230 has entered the distal central lumen 601d from the subintimal space.

Figure 20:
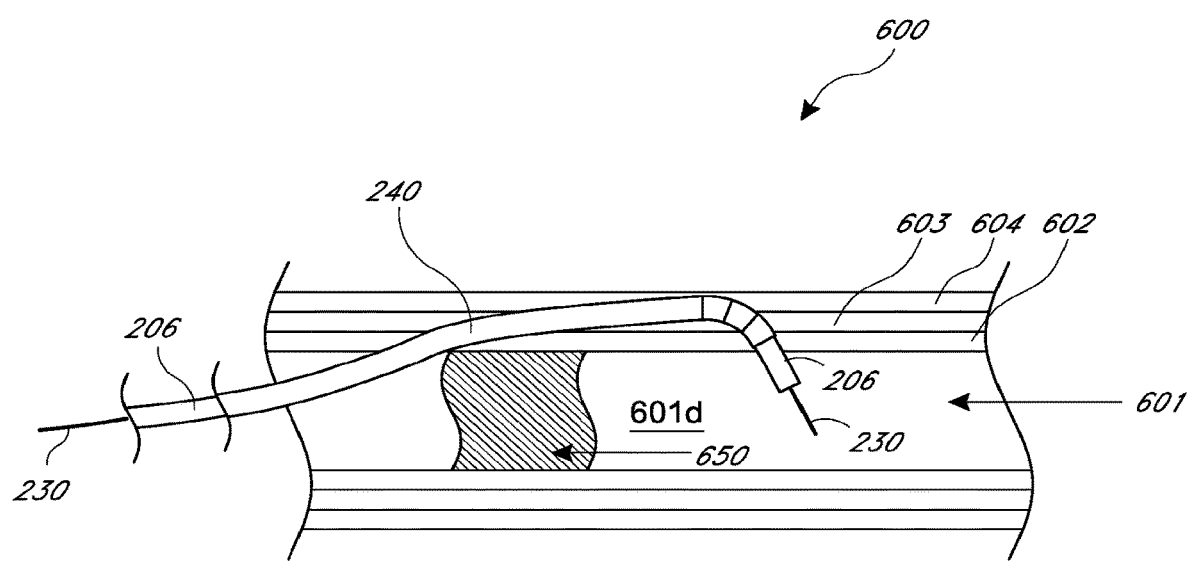

Turning to FIG. 20, the method continues by advancing the dilator 206 over the ultrasound transmission member 230, through the sheath 240, and into the distal central lumen 601d. The dilator 206 may have a distal portion having a similar profile to the ultrasound transmission member 230 such that the distal portion of the dilator 206 can facilitate the following of the ultrasound transmission member 230 from the extraluminal or subintimal space and into the central lumen 601. In this way, the dilator 206 serves as a transition member between the relatively small diameter of the ultrasound transmission member 230 and the relatively larger diameter of the sheath 240. In some embodiments, at least a portion of the dilator 206 is tapered in a direction towards the distal tip of the dilator 206.

In one embodiment, the dilator 206 is inserted into the sheath 240 before the ultrasound transmission member 230 is inserted. That is to say, after the guidewire 800 is removed from the sheath 240, the dilator 206 is advanced through the sheath 240. Next, the ultrasound transmission member 230 is advanced through the dilator 206. The ultrasound transmission member 230 can then be advanced through the extraluminal space so as to re-enter the distal central lumen 601d through the vessel wall.

In some embodiments, the dilator 206 and ultrasound transmission member 230 are sized such that the ultrasound transmission member 230 only advances outside the distal end of the dilator 206 by a maximum distance (for example, about 5 mm or less). For example, the ultrasound transmission member 203 and the dilator 206 can be sized and/or tapered in such a way that the ultrasound transmission member 203 extends beyond the end of the dilator 206 a predetermined amount before the walls of the dilator 206 prevent further advancement of the ultrasound transmission member 230. In this way, the dilator 206 can serve to prevent the ultrasound transmission member 230 from being advanced too far distally, thus minimizing the potential of the ultrasound transmission member 230 piercing the opposite vessel wall.

Figure 21:
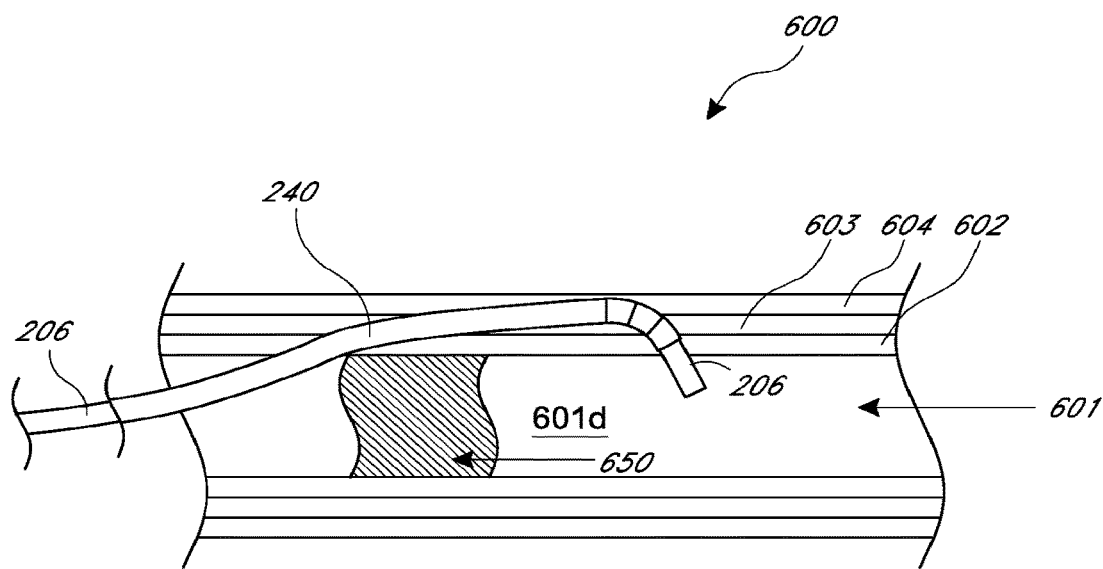
Figure 22:
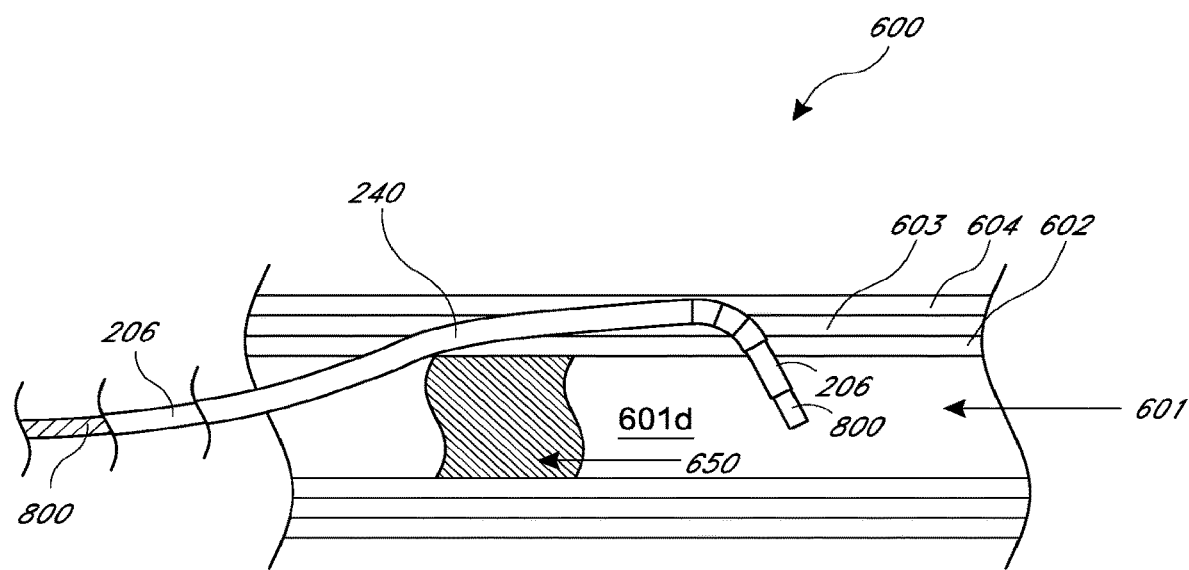
Figure 23:
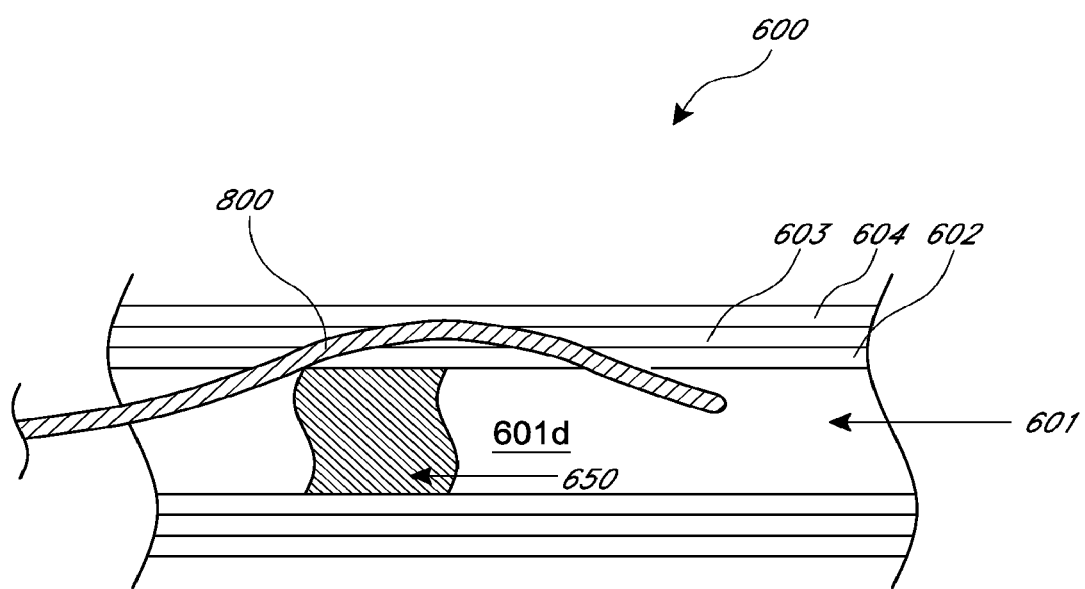

Turning to FIG. 21, the ultrasound transmission member 203 can be removed after the dilator 206 is positioned in the distal central lumen 601d. Next, as shown in FIG. 22, the guidewire 800 can be advanced through the dilator 206 and into the distal central lumen 601d. The sheath 240 and dilator 206 can then be removed as shown in FIG. 23 leaving the distal end of the guidewire 800 in the distal central lumen 601d. The sheath 240 and/or 206 dilator can be removed together or separately in any order.

Figure 24:
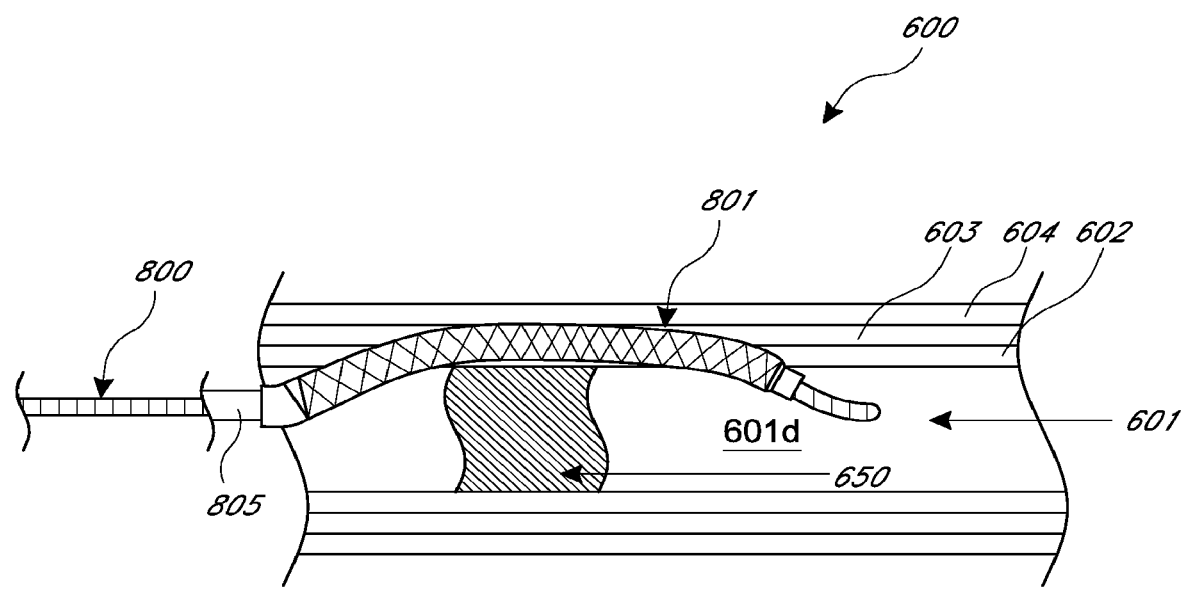
Figure 25:
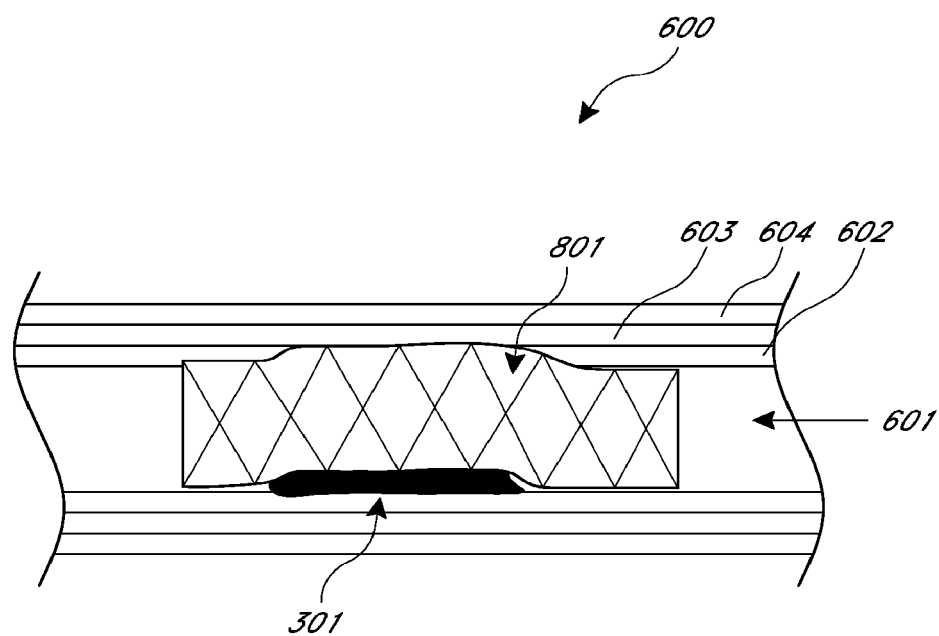

As shown in FIG. 24, once the guidewire 800 has crossed over the occlusion 650, a balloon catheter 805 with a stent 801 can be advanced over the guidewire 800 and positioned within the region of the occlusion 650. The balloon catheter 805 can then be expanded deploying the stent 801. The balloon catheter 805 and guidewire 800 can then be removed, leaving the fully deployed stent 805 in the vessel as shown in FIG. 25.

The various embodiments described above thus provide a number of ways to provide for treatment of occluded vessels. In addition, the techniques described may be broadly applied for use with a variety of medical procedures. Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and devices have been disclosed in the context of certain embodiments and examples, it will be understood by those skilled in the art that these techniques and devices may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above, but should be determined only by a fair reading of the claims that follow.

What is claimed is:

1. A method for operating an ultrasonic reentry device, comprising:
   providing an ultrasound transmission member having a proximal end and a distal end;
   providing a catheter body having a lumen surrounding the ultrasound transmission member;
   providing a dilator slidably disposed within the lumen of the catheter body, the dilator surrounding the ultrasound transmission member;
   exposing the distal end of the ultrasound transmission member from a distal end of the dilator; and
   providing a sheath disposed over the dilator, the catheter body, and the ultrasound transmission member.

2. The method of claim 1, wherein exposing the distal end protrudes the ultrasound transmission member 1-5 mm past the distal end of the dilator.

3. The method of claim 1, comprising: exposing a distal end of the dilator from a distal end of the sheath.

4. The method of claim 1, comprising:
   articulating a distal end of the sheath.

5. The method of claim 4, wherein the act of articulating comprises articulating the distal end of the sheath up to 90 degrees away from a longitudinal axis.

6. The method of claim 4, comprising:
   exposing the dilator and the ultrasound transmission member from the distal end of the sheath;
   articulating the distal end of the sheath in a first lateral direction;
   advancing a relative position of the combination of the sheath, the dilator, and the ultrasound transmission member;
   articulating the distal end of the sheath in a second lateral direction different from the first lateral direction; and
   further advancing the relative position of the combination of the sheath, the dilator, and the ultrasound transmission member.

7. The method of claim 6, comprising transmitting an ultrasonic vibration to the distal end of the ultrasound transmission member prior to at least one of the advancing step and the further advancing step.

8. The method of claim 6, comprising visualizing a distal portion of the sheath using fluoroscopy during each of the articulating and advancing steps.

9. The method of claim 6, comprising removing the ultrasound transmission member and the dilator from the sheath following the step of further advancing.

10. The method of claim 6, comprising:
    removing the ultrasound transmission member from the dilator following the step of further advancing; and
    inserting a guidewire through the dilator.

11. A method for operating an ultrasonic reentry device, comprising:
    providing a catheter body having a lumen;
    providing an ultrasound transmission member disposed in the lumen, the ultrasound transmission member having a taper to a needle-like distal end;
    disposing a dilator over the ultrasound transmission member, with the catheter body overlapping the dilator;
    providing a sheath disposed over the dilator, the catheter body, and the ultrasound transmission member; and
    articulating a distal end of the sheath to position the distal end of the ultrasound transmission member and a distal end of the dilator.

12. The method of claim 11, wherein the act of articulating comprises articulating the distal end of the sheath up to 90 degrees away from a longitudinal axis.

13. The method of claim 11, comprising exposing a distal end of the dilator from the distal end of the sheath.

14. The method of claim 13, comprising exposing the distal end of the ultrasound transmission member from the distal end of the dilator.

15. The method of claim 14, wherein exposing the distal end protrudes the ultrasound transmission member 1-5 mm past the distal end of the dilator.

16. The method of claim 11, comprising:
    exposing the dilator and the ultrasound transmission member from the distal end of the sheath;
    articulating the distal end of the sheath in a first lateral direction;
    advancing a relative position of the combination of the sheath, dilator, and the ultrasound transmission member;
    articulating the distal end of the sheath in a second lateral direction different from the first lateral direction;

transmitting an ultrasonic vibration to the distal end of the ultrasound transmission member; and further advancing the relative position of the combination of the sheath, the dilator, and the ultrasound transmission member.

17. The method of claim 16, comprising transmitting an ultrasonic vibration to the distal end of the ultrasound transmission member prior to the first step of advancing.

18. The method of claim 16, comprising visualizing a distal portion of the sheath using fluoroscopy during each of the articulating and advancing steps.

19. The method of claim 16, comprising removing the ultrasound transmission member and the dilator from the sheath following the step of further advancing.

20. The method of claim 16, comprising:

removing the ultrasound transmission member from the dilator following the step of further advancing; and inserting a guidewire through the dilator.

\* \* \* \* \*